US012629373B2

(12) United States Patent
Dabdoub

(10) Patent No.: US 12,629,373 B2
(45) Date of Patent: May 19, 2026

(54) DIETARY MACRO/MICRONUTRITIONAL COMPOSITIONS AND APPLICATIONS THEREOF

(71) Applicant: Atif Dabdoub, Atlanta, GA (US)

(72) Inventor: Atif Dabdoub, Atlanta, GA (US)

(73) Assignee: Atif Dabdoub, Atlanta, GA (US)

( * ) Notice: Subject to any disclaimer, the term of this patent is extended or adjusted under 35 U.S.C. 154(b) by 0 days.

(21) Appl. No.: 18/935,743

(22) Filed: Nov. 4, 2024

(65) Prior Publication Data

US 2025/0057842 A1    Feb. 20, 2025

Related U.S. Application Data

(63) Continuation-in-part of application No. PCT/US2023/066587, filed on May 4, 2023.
(Continued)

(51) Int. Cl.
*A61K 31/00*          (2006.01)
*A61K 31/122*        (2006.01)
(Continued)

(52) U.S. Cl.
CPC ............ *A61K 31/51* (2013.01); *A61K 31/122* (2013.01); *A61K 31/197* (2013.01);
(Continued)

(58) Field of Classification Search
CPC ....................................................... A61K 31/00
See application file for complete search history.

(56) References Cited

U.S. PATENT DOCUMENTS 10,828,313 B2    11/2020  Salomonsson et al.
2013/0344167 A1    12/2013  Chery et al.
(Continued)

FOREIGN PATENT DOCUMENTS

GB          2585619  A      1/2021
JP          H10273442 A     10/1998
(Continued)

OTHER PUBLICATIONS

Legman et al., "Investigating the causes for decreased levels of glutathione in individuals with type II diabetes," Plos One, doc. No. 0118436, 19 pp., 2015.*
(Continued)

*Primary Examiner* — Rosanne Kosson
(74) *Attorney, Agent, or Firm* — Thomas | Horstemeyer, LLP

(57)          ABSTRACT

Provided herein are compositions composed of a plurality of minerals and vitamins that provide numerous health benefits and quality of life to subjects in need thereof. Also described herein are kits composed of the compositions described herein with a marine omega 3 fatty acid, coenzyme Q10, or a combination thereof. In one aspect, the compositions described herein can treat a subject diagnosed with prediabetes, type 1 diabetes, type 2 diabetes or insulin uptake. In another aspect, the compositions described herein can increase the performance of athletes by relaxing and dilating blood vessels, thus improve circulation as well as shorten the time of recovery after exercises or games. In another aspect, the compositions described herein can improve the well-being and immune response system. It also improves the human system against bacterial and fungal infections. In another aspect, the compositions described herein can treat myalgic encephalomyelitis in a subject. In another aspect, the compositions described herein can reduce or prevent one or more symptoms of Crohn's disease in a subject. In another aspect, the compositions described herein can enhance one or more physical properties of a subject after exercise.

14 Claims, 4 Drawing Sheets

Related U.S. Application Data

(60) Provisional application No. 63/416,767, filed on Oct. 17, 2022, provisional application No. 63/364,210, filed on May 5, 2022.

(51) Int. Cl.

| | |
|---|---|
| *A61K 31/197* | (2006.01) |
| *A61K 31/198* | (2006.01) |
| *A61K 31/20* | (2006.01) |
| *A61K 31/205* | (2006.01) |
| *A61K 31/375* | (2006.01) |
| *A61K 31/381* | (2006.01) |
| *A61K 31/4188* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/593* | (2006.01) |
| *A61K 31/714* | (2006.01) |
| *A61K 33/04* | (2006.01) |
| *A61K 33/06* | (2006.01) |
| *A61K 33/22* | (2006.01) |
| *A61K 33/24* | (2019.01) |
| *A61K 33/26* | (2006.01) |
| *A61K 33/30* | (2006.01) |
| *A61K 33/32* | (2006.01) |
| *A61K 33/34* | (2006.01) |
| *A61K 38/06* | (2006.01) |
| *A61K 47/36* | (2006.01) |
| *A61K 47/46* | (2006.01) |
| *A61P 3/10* | (2006.01) |

(52) U.S. Cl.
CPC ............ *A61K 31/198* (2013.01); *A61K 31/20* (2013.01); *A61K 31/205* (2013.01); *A61K 31/375* (2013.01); *A61K 31/381* (2013.01); *A61K 31/4188* (2013.01); *A61K 31/4415* (2013.01); *A61K 31/455* (2013.01); *A61K 31/519* (2013.01); *A61K 31/525* (2013.01); *A61K 31/593* (2013.01); *A61K 31/714* (2013.01); *A61K 33/04* (2013.01); *A61K 33/06* (2013.01); *A61K 33/22* (2013.01); *A61K 33/24* (2013.01); *A61K 33/26* (2013.01); *A61K 33/30* (2013.01); *A61K 33/32* (2013.01); *A61K 33/34* (2013.01); *A61K 38/063* (2013.01); *A61K 47/36* (2013.01); *A61K 47/46* (2013.01); *A61P 3/10* (2018.01)

(56) References Cited

U.S. PATENT DOCUMENTS

| | | |
|---|---|---|
| 2014/0161784 A1 | 6/2014 | Westerlund et al. |
| 2016/0101081 A1 | 4/2016 | Pan et al. |
| 2016/0235822 A1 | 8/2016 | Holstein et al. |
| 2017/0056463 A1* | 3/2017 | Cohen ..................... A23L 33/40 |
| 2021/0353578 A1 | 11/2021 | Dabdoub |

FOREIGN PATENT DOCUMENTS

| | | |
|---|---|---|
| WO | 2020231906 A1 | 11/2020 |
| WO | 2021142157 A1 | 7/2021 |

OTHER PUBLICATIONS

Jain et al., "Vitamin E, its beneficial role in diabetes mellitus (DM) and its complications," Journal of Clinical and Diagnostic Research, 6(10):1624-1628, 2012.*

Nemzer et al., "Betalainic and nutritional profiles of pigment-enriched red beet root (*Beta vulgaris* L.) dried extracts," Food Chemistry 127:42-53, 2011.*

International Search Report for application PCT/US2023/066587 mailed Sep. 12, 2023.

* cited by examiner

DIETARY MACRO/MICRONUTRITIONAL COMPOSITIONS AND APPLICATIONS THEREOF

CROSS-REFERENCE TO RELATED APPLICATIONS

This application is a continuation-in-part of international application number PCT/US2023/066587, filed May 4, 2023, which claims the benefit of and priority to U.S. Provisional Patent Application Nos. 63/364,210 filed on May 5, 2022, and 63/416,767 filed on Oct. 17, 2022, the contents of which are incorporated by reference herein in their entireties.

BACKGROUND

Many diseases are linked to inflammations and/or deficiencies in the immune system, which can lead to damage of vital organs in the body. There are also less severe diseases or temporary illnesses that can be caused by a less potent immune defense system. By administering well targeted supplements the immune system can be boosted.

Two major patient categories are especially exposed—patients with diabetes and patients with advanced kidney failure. Diabetes is one of the most widespread diseases in the world and persons with end-stage kidney disease being treated on dialysis are quite costly on an annual basis. Both these categories of patients are creating a significant cost burden on societies; thus, any improvements for these patient categories provide both an advantage for the patient and the society.

SUMMARY

Provided herein are compositions composed of a plurality of minerals and vitamins that provide numerous health benefits and quality of life to subjects in need thereof. Also described herein are kits composed of the compositions described herein with a marine omega 3 fatty acid, coenzyme Q10, or a combination thereof. In one aspect, the compositions described herein can treat a subject diagnosed with prediabetes, type 1 diabetes, type 2 diabetes or insulin uptake. In another aspect, the compositions described herein can increase the performance of athletes by relaxing and dilating blood vessels, thus improve circulation as well as shorten the time of recovery after exercises or games. In another aspect, the compositions described herein can improve the well-being and immune response system. It also improves the human system against bacterial and fungal infections. In another aspect, the compositions described herein can treat myalgic encephalomyelitis in a subject. In another aspect, the compositions described herein can reduce or prevent one or more symptoms of Crohn's disease in a subject. In another aspect, the compositions described herein can enhance one or more physical properties of a subject after exercise.

The advantages of the materials, methods, and devices described herein will be set forth in part in the description that follows or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figure 1:
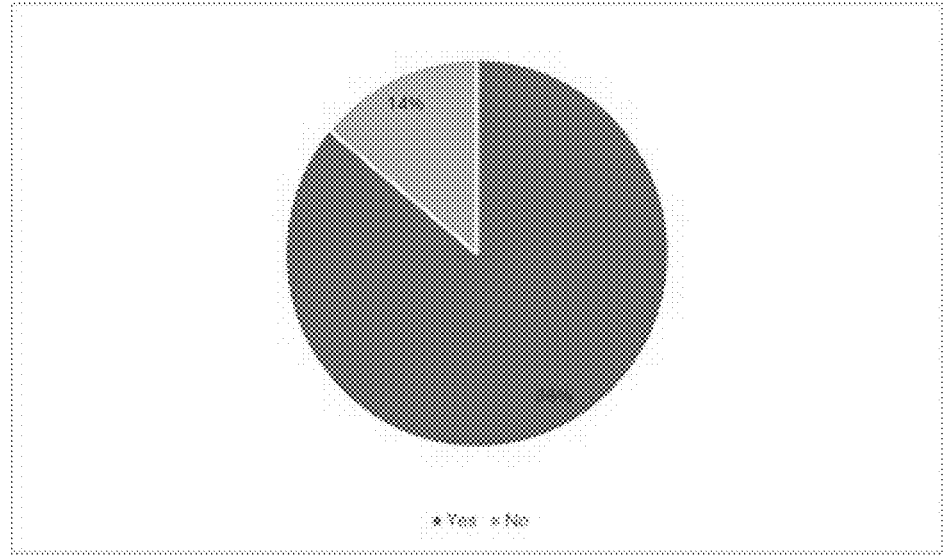
FIG. 1 shows participants who experienced a positive change in two or more areas when taking RenuSport: recovery, training soreness, endurance and lactic acidity.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

It must be noted that, as used in the specification and the appended claims, the singular forms "a," "an," and "the" include plural referents unless the context clearly dictates otherwise. Thus, for example, reference to "a citrus bioflavonoid" includes mixtures of two or more citrus bioflavonoids, and the like.

"Optional" or "optionally" means that the subsequently described event or circumstance can or cannot occur, and that the description includes instances where the event or circumstance occurs and instances where it does not. For example, the nutritional compositions described herein may optionally contain turmeric, where the turmeric may or may not be present.

"Unit dose" refers to a discrete amount of a composition described herein to be administered to a subject. The compositions disclosed herein are packaged into discrete dosages each containing predetermined quantities of active compounds calculated based on the needs and medical history of the subject.

A "pharmaceutically-acceptable compound" is used to refer to a neutral complex. In some aspects, a pharmaceutically-acceptable compound may be more economical to produce, may have increased chemical stability, may allow manipulation of the compound's pharmacokinetics and bioavailability, may make the compound easier to administer, or a combination thereof. In a further aspect, a pharmaceutically-acceptable compound can alter a compound's dissolution or solubility. In one aspect, the pharmaceutically-acceptable compound can be an ionic compound. For example, the pharmaceutically-acceptable compound can be the reaction product between an organic acid (e.g., citric acid) and base (e.g., calcium hydroxide) to produce the ionic compound calcium citrate.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrobromic, hydrochloric, nitric, carbonic, monohydrogencarbonic, phosphoric, monohydrogenphosphoric, dihydrogenphosphoric, and the like, as well as the salts derived from relatively nontoxic organic acids like acetic, propionic, isobutyric, succinic, and lactic. Also included are salts of amino acids such as arginate and the like, and salts of organic acids like glucuronic or galacturonic acids and the like.

As used herein, the terms "treating" and "treatment" can refer generally to obtaining a desired pharmacological and/or physiological effect. The effect can be therapeutic in terms of a partial or complete cure of a disease, condition, symptom or adverse effect attributed to the disease, disorder, or condition. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

The term "reduce" as used herein is defined as decreasing the likelihood of the occurrence of one or more symptoms using the compositions described herein when compared to the same symptom in the absence of using the compositions described herein.

The term "prevent" as used herein is defined as eliminating or reducing the likelihood of the occurrence of one or more symptoms using the compositions described herein when compared to the same symptom in the absence of using the compositions described herein.

The term "promote" as used herein is defined as increasing the likelihood of improving one or more symptoms using the compositions described herein when compared to the same symptom in the absence of using the compositions described herein.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used interchangeably herein, "subject," "individual," or "patient" can refer to a vertebrate organism, such as a mammal (e.g. human).

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range. Thus, for example, if a component is in an amount of about 1%, 2%, 3%, 4%, or 5%, where any value can be a lower and upper endpoint of a range, then any range is contemplated between 1% and 5% (e.g., about 1% to about 3%, about 2% to about 4%, etc.).

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5 and are present in such ratio regardless of whether additional components are contained in the compound.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference to each individual and collective combination and permutation of these compounds may not be explicitly disclosed, each is specifically contemplated and described herein. For example, if a water soluble vitamin is disclosed and discussed and a number of different minerals are discussed, each and every combination of water soluble vitamin and mineral that is possible is specifically contemplated unless specifically indicated to the contrary. For example, if a class of water soluble vitamins A, B, and C are disclosed, as well as a class of minerals D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered from disclosure of A, B, and C; D, E, and F; and the example combination of A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such combination is specifically contemplated and should be considered disclosed.

Compositions

The compositions described herein include a plurality of vitamins and minerals that provide numerous health benefits as discussed in detail below. In one aspect, the compositions disclosed herein include one or more water soluble vitamins.

B Complex Vitamins

In one aspect, the formulations disclosed herein include one or more B vitamins. In this aspect, B vitamins generally act as cofactors or coenzymes or precursors needed to make cofactors or coenzymes. In a further aspect, B vitamins are not stored in the body and must be regularly supplied by dietary or other means to avoid deficiency. In one aspect, co-supplementation of vitamins $B_6$, $B_9$, and $B_{12}$ along with iron is especially effective against osteoporosis and anemia while also improving immune function. In a further aspect, all B complex vitamins can be used instead of just one or two.

In another aspect, low levels of B vitamins can affect the manufacture of neurotransmitters and contribute to stress and anxiety. In this aspect, supplementation of B vitamins can reduce stress related to their deficiency. In one aspect, low levels of B vitamins are caused by chronic kidney dialysis, the use of diuretics, and overconsumption of refined carbohydrates, since digestion of many carbohydrates requires the use of B vitamins. In one aspect, inadequate B vitamin intake is linked to blood sugar surges in patients who consume too many refined carbohydrates.

In one aspect, thiamin, or vitamin $B_1$, is included in the compositions disclosed herein. In this aspect, thiamin may be important to nerve and muscle health, production of hydrochloric acid in the stomach, and treatment of constipation and fatigue, as well as assisting digestion of some carbohydrates and proteins. In one aspect, the thiamine source is thiamine mononitrate.

In one aspect, vitamin $B_1$ is present in an amount of from about 0.10 weight percent to about 0.50 weight percent of the composition, or about 0.10 weight percent, about 0.15 weight percent, about 0.20 weight percent, about 0.25 weight percent, about 0.30 weight percent, about 0.35 weight percent, about 0.40 weight percent, about 0.45 weight percent, or about 0.50 weight percent, where any value can be a lower and upper endpoint of a range (e.g., about 0.20 weight percent to about 0.30 weight percent). In another aspect, the amount of vitamin $B_1$ present per unit dose is from about 0.50 weight percent to about 3.00 weight percent of the composition, or about 0.50 weight percent, about 1.00 weight percent, about 1.50 weight percent, about 2.00 weight percent, about 2.50 weight percent, or about 3.00 weight percent, where any value can be a lower and upper endpoint of a range (e.g., about 1.00 weight percent to about 2.00 weight percent).

In another aspect, riboflavin, or vitamin $B_2$, is included in the compositions disclosed herein. In this aspect, riboflavin may be important for growth, red blood cell production, and eye health, as well as assisting in the digestion of some carbohydrates, fats, ketone bodies, and proteins.

In one aspect, vitamin $B_2$ is present in an amount of from about 0.10 weight percent to about 0.50 weight percent of the composition, or about 0.10 weight percent, about 0.15 weight percent, about 0.20 weight percent, about 0.25 weight percent, about 0.30 weight percent, about 0.35 weight percent, about 0.40 weight percent, about 0.45 weight percent, or about 0.50 weight percent, where any value can be a lower and upper endpoint of a range (e.g., about 0.20 weight percent to about 0.30 weight percent). In another aspect, the amount of vitamin $B_2$ present per unit dose is from about 0.50 weight percent to about 3.00 weight percent of the composition, or about 0.50 weight percent, about 1.00 weight percent, about 1.50 weight percent, about 2.00 weight percent, about 2.50 weight percent, or about 3.00 weight percent, where any value can be a lower and upper endpoint of a range (e.g., about 1.00 weight percent to about 2.00 weight percent).

In still another aspect, nicotinic acid or nicotinamide, also known as niacinamide or vitamin $B_3$, is included in the compositions disclosed herein. Further in this aspect, vitamin $B_3$ is important to digestive system health and may assist in the digestion of some carbohydrates, as well as in the production of various sex and stress-related hormones. Still further in this aspect, niacin may be useful in reducing cholesterol levels in the blood.

In one aspect, vitamin $B_3$ is present in an amount of from about 0.10 weight percent to about 0.50 weight percent of the composition, or about 0.10 weight percent, about 0.15 weight percent, about 0.20 weight percent, about 0.25 weight percent, about 0.30 weight percent, about 0.35 weight percent, about 0.40 weight percent, about 0.45 weight percent, or about 0.50 weight percent, where any value can be a lower and upper endpoint of a range (e.g., about 0.20 weight percent to about 0.40 weight percent). In another aspect, the amount of vitamin $B_3$ present per unit dose is from about 1.00 weight percent to about 3.00 weight percent of the composition, or about 1.00 weight percent, about 1.25 weight percent, about 1.50 weight percent, about 1.75 weight percent, about 2.00 weight percent, about 2.25 weight percent, about 2.75 weight percent, or about 3.00 weight percent, where any value can be a lower and upper endpoint of a range (e.g., about 2.00 weight percent to about 2.50 weight percent).

In one aspect, the compositions disclosed herein include pantothenic acid, or vitamin $B_5$. In this aspect, pantothenic acid may be important for red blood cells production, digestive system health, adrenal gland health, and the digestion of some carbohydrates.

In one aspect, vitamin $B_5$ is present in an amount of from about 0.010 weight percent to about 0.50 weight percent of the composition, or about 0.010 weight percent, about 0.05 weight percent, about 0.10 weight percent, about 0.15 weight percent, about 0.20 weight percent, about 0.25 weight percent, about 0.30 weight percent, about 0.35 weight percent, about 0.40 weight percent, about 0.45 weight percent, or about 0.50 weight percent, where any value can be a lower and upper endpoint of a range (e.g., about 0.20 weight percent to about 0.30 weight percent). In another aspect, the amount of vitamin $B_5$ present per unit dose is from about 0.10 weight percent to about 2.00 weight percent of the composition, or about 0.10 weight percent, about 0.25 weight percent, about 0.50 weight percent, about 0.75 weight percent, about 1.00 weight percent, about 1.25 weight percent, about 1.50 weight percent, about 1.75 weight percent, or about 2.00 weight percent, where any value can be a lower and upper endpoint of a range (e.g., about 0.75 weight percent to about 1.25 weight percent).

In another aspect, the compositions disclosed herein include pyridoxal phosphate (also occurring as pyridoxine), or vitamin $B_6$. Further in this aspect, pyridoxal phosphate may be important for brain health and the production of red blood cells and immune system cells. In a further aspect, deficiencies in vitamin $B_6$ have been linked to diabetes, nervous system disorders, and heart disease.

In one aspect, vitamin $B_6$ is present in an amount of from about 0.01 weight percent to about 0.50 weight percent of the composition, or about 0.01 weight percent, about 0.05 weight percent, about 0.10 weight percent, about 0.15 weight percent, about 0.20 weight percent, about 0.25 weight percent, about 0.30 weight percent, about 0.35 weight percent, about 0.40 weight percent, about 0.45 weight percent, or about 0.50 weight percent, where any value can be a lower and upper endpoint of a range (e.g., about 0.05 weight percent to about 0.10 weight percent). In another aspect, the amount of vitamin $B_6$ present per unit dose is from about 0.10 weight percent to about 2.00 weight percent of the composition, or about 0.10 weight percent, about 0.25 weight percent, about 0.50 weight percent, about 0.75 weight percent, about 1.00 weight percent, about 1.25 weight percent, about 1.50 weight percent, about 1.75 weight percent, or about 2.00 weight percent, where any value can be a lower and upper endpoint of a range (e.g., about 0.25 weight percent to about 0.75 weight percent).

In still another aspect, the compositions disclosed herein include biotin, or vitamin $B_7$. In a further aspect, biotin is important to various aspects of metabolism and may be important in strengthening the hair and nails as well as in the metabolism of fats and amino acids. In one aspect, the biotin source is molecular biotin.

In one aspect, vitamin $B_7$ is present in an amount of from about 0.10 weight percent to about 1.00 weight percent of the composition, or about 0.10 weight percent, about 0.20 weight percent, about 0.30 weight percent, about 0.40 weight percent, about 0.50 weight percent, about 0.60 weight percent, about 0.70 weight percent, about 0.80 weight percent, about 0.90 weight percent, or about 1.00 weight percent, where any value can be a lower and upper endpoint of a range (e.g., about 0.20 weight percent to about 0.80 weight percent). In another aspect, the amount of vitamin $B_7$ present per unit dose is from about 0.10 weight percent to about 3.00 weight percent of the composition, or about 0.10 weight percent, about 0.25 weight percent, about 0.50 weight percent, about 0.75 weight percent, about 1.00 weight percent, about 1.25 weight percent, about 1.50 weight percent, about 1.75 weight percent, about 2.00 weight percent, about 2.25 weight percent, about 2.50 weight percent, about 2.75 weight percent, or about 3.00 weight percent, where any value can be a lower and upper endpoint of a range (e.g., about 1.75 weight percent to about 2.25 weight percent).

In one aspect, the compositions disclosed herein include folate, also known as folic acid or vitamin $B_9$. Further in this aspect, folic acid may be important for brain function, mental health, red blood cells production, and production of nucleic acids. In one aspect, the folate source is folic acid.

In one aspect, vitamin $B_9$ is present in an amount of from about 0.001 weight percent to about 0.10 weight percent of the composition, or about 0.001 weight percent, about 0.005 weight percent, about 0.010 weight percent, about 0.020 weight percent, about 0.030 weight percent, about 0.040 weight percent, about 0.050 weight percent, about 0.060 weight percent, about 0.070 weight percent, about 0.080 weight percent, about 0.090 weight percent, or about 0.10 weight percent, where any value can be a lower and upper endpoint of a range (e.g., about 0.0050 weight percent to about 0.010 weight percent). In another aspect, the amount of vitamin $B_9$ present per unit dose is from about 0.010 weight percent to about 0.10 weight percent of the composition, or about 0.010 weight percent, about 0.020 weight percent, about 0.030 weight percent, about 0.040 weight percent, about 0.050 weight percent, about 0.060 weight percent, about 0.070 weight percent, about 0.080 weight percent, about 0.090 weight percent, or about 0.10 weight percent, where any value can be a lower and upper endpoint of a range (e.g., about 0.030 weight percent to about 0.050 weight percent).

In another aspect, cobalamin, or vitamin $B_{12}$, is included in the formulations disclosed herein. Further in this aspect, the cobalamin may be present as the cyanocobalamin, hydroxycobalamin, adenosylcobalamin, or methylcobalamin form. In another aspect, cobalamin is important to nervous system health, the production of red blood cells, and synthesis of nucleic acids. In a further aspect, cobalamin works synergistically with folate with respect to red blood cell production. In one aspect, the cobalamin source is cyanocobalamin.

In one aspect, vitamin $B_{12}$ is present in an amount of from about 0.10 weight percent to about 2.00 weight percent of the composition, or about 0.10 weight percent, about 0.25 weight percent, about 0.50 weight percent, about 0.75 weight percent, about 1.00 weight percent, about 1.25 weight percent, about 1.50 weight percent, about 1.75 weight percent, or about 2.00 weight percent, where any value can be a lower and upper endpoint of a range (e.g., about 0.70 weight percent to about 1.00 weight percent). In another aspect, the amount of vitamin $B_{12}$ present per unit dose is from about 1.0 weight percent to about 10.00 weight percent of the composition, or about 1.0 weight percent, about 1.5 weight percent, about 2.0 weight percent, about 2.5 weight percent, about 3.0 weight percent, about 3.5 weight percent, about 4.0 weight percent, about 4.5 weight percent, about 5.0 weight percent, about 5.5 weight percent, about 6.0 weight percent, about 6.5 weight percent, about 7.0 weight percent, about 7.5 weight percent, about 8.0 weight percent, about 8.5 weight percent, about 9.0 weight percent, about 9.5 weight percent, or about 10.0 weight percent, where any value can be a lower and upper endpoint of a range (e.g., about 4.0 weight percent to about 6.0 weight percent).

Vitamin C

In one aspect, the formulations disclosed herein include ascorbic acid or vitamin C. In a further aspect, vitamin C is important to the immune system, collagen production, and wound healing. Further in this aspect, vitamin C is needed for the biosynthesis of hydroxyproline, which is important in the synthesis of collagen, osteoid, and dentin.

In a further aspect, vitamin C is a potent antioxidant that can fight free radical damage. In a still further aspect, vitamin C may assist with the uptake of non-heme iron. In yet another aspect, vitamin C helps to protect folate from oxidative damage.

In one aspect, vitamin C is present in an amount of from about 1.00 weight percent to about 5.00 weight percent of the composition, or about 1.00 weight percent, about 1.50 weight percent, about 2.00 weight percent, about 2.50 weight percent, about 3.00 weight percent, about 3.50 weight percent, about 4.00 weight percent, about 4.50 weight percent, or about 5.00 weight percent, where any value can be a lower and upper endpoint of a range (e.g., about 1.00 weight percent to about 2.00 weight percent). In another aspect, the amount of vitamin $B_{12}$ present per unit dose is from about 1.0 weight percent to about 10.00 weight percent of the composition, or about 1.0 weight percent, about 1.5 weight percent, about 2.0 weight percent, about 2.5 weight percent, about 3.0 weight percent, about 3.5 weight percent, about 4.0 weight percent, about 4.5 weight percent, about 5.0 weight percent, about 5.5 weight percent, about 6.0 weight percent, about 6.5 weight percent, about 7.0 weight percent, about 7.5 weight percent, about 8.0 weight percent, about 8.5 weight percent, about 9.0 weight percent, about 9.5 weight percent, or about 10.0 weight percent, where any value can be a lower and upper endpoint of a range (e.g., about 6.0 weight percent to about 7.0 weight percent).

Vitamins A, E, and K

In one aspect, vitamins A, E, and K can accumulate to toxic levels in body tissue of patients undergoing dialysis. Handbook of Nonprescription Drugs, 11$^{th}$ edition, 1996, American Pharmaceutical Association. 2215 Constitution Avenue, NW, Washington, DC 20037. Chapter 19, Nutritional Products, page 366. Further in this aspect, supplementation of these vitamins for kidney dialysis patients is contraindicated. In another aspect, the compositions disclosed herein do not include vitamins A, E, and K.

Vitamin D

In another aspect, vitamin $D_3$ is a fat-soluble vitamin that is usually activated by healthy or well-functioning kidneys. In one aspect, in the case of kidney failure, the body cannot produce enough vitamin $D_3$ and it should be supplemented in patients with kidney failure. However, in another aspect, a patient's medical providers may decide vitamin $D_3$ supplementation is not required and/or would cause further harm. In any of the above aspects, the composition may or may not include a source of vitamin $D_3$, to be given at the discretion of healthcare providers on a case-by-case basis. In one aspect, vitamin $D_3$ is derived from lanolin.

In one aspect, when vitamin $D_3$ is included in the formulations disclosed herein, it may improve bone health and immune system function and may protect against certain cancers. In a further aspect, vitamin $D_3$ can increase calcium and phosphate absorption from the small intestine, is important in bone mineralization, and maintains proper calcium and phosphorus levels in the serum. Handbook of Nonprescription Drugs, 11$^{th}$ edition, 1996, American Pharmaceutical Association. 2215 Constitution Avenue, NW, Washington, DC 20037. Chapter 19, Nutritional Products, page 368.

In one aspect, vitamin $D_3$ is present in an amount of from about 0.01 weight percent to about 0.50 weight percent of the composition, or about 0.01 weight percent, about 0.05 weight percent, about 0.10 weight percent, about 0.15 weight percent, about 0.20 weight percent, about 0.25 weight percent, about 0.30 weight percent, about 0.35 weight percent, about 0.40 weight percent, about 0.45 weight percent, or about 0.50 weight percent, where any value can be a lower and upper endpoint of a range (e.g., about 0.05 weight percent to about 0.20 weight percent). In another aspect, the amount of vitamin $D_3$ present per unit dose is from about 0.10 weight percent to about 1.00 weight percent of the composition, or about 0.10 weight percent, about 0.20 weight percent, about 0.30 weight percent, about 0.40 weight percent, about 0.50 weight percent, about 0.60 weight percent, about 0.70 weight percent, about 0.80 weight percent, about 0.90 weight percent, or about 1.00 weight percent, where any value can be a lower and upper endpoint of a range (e.g., about 0.50 weight percent to about 0.70 weight percent).

As used herein, a mineral is an inorganic element that is obtained from food or supplementation and is required for the functioning of the human body. Minerals include, but are not limited to, calcium, chromium, copper, iron, magnesium, manganese, molybdenum, nickel, potassium, selenium, sodium, vanadium, cobalt, and zinc. In one aspect, a mineral can act as a cofactor. In other aspects, minerals can be used for cell signaling, or can be an essential structural component of the body (e.g., calcium in bone), or can associate with proteins, nucleic acids, lipids, and carbohydrates to maintain secondary, tertiary, and quaternary structures.

In another aspect, the mineral can be part of a chelate complex. Chelates have a cyclic structure in which a central metallic ion is held tight via covalent-coordinate bonds to form a coordinate compound, or, a chelate complex. Furthermore, chelates occur abundantly in nature; for example, chlorophyll complexed with magnesium, hemoglobin with iron, Vitamin B12 with cobalt hemocyanin with copper as well as enzymes that contain vanadium or molybdenum.

Calcium

In one aspect, the formulations disclosed herein include a pharmaceutically-acceptable compound of calcium. In a further aspect, calcium supplementation can be useful in preventing osteoporosis since calcium is a major component of bones and teeth. In a still further aspect, calcium's absorption and effects are enhanced or aided by vitamin $D_3$ and parathyroid hormone. In still another aspect, calcium may be important to B complex vitamin absorption and is important to the functional integrity of many cells. In yet another aspect, calcium requirements may increase with increased protein consumption.

In one aspect, the calcium is provided as an ionic compound of calcium. Examples of such compounds include, but are not limited to, calcium citrate, calcium citrate tetrahydrate, calcium lactate pentahydrate, calcium ascorbate, calcium carbonate, or calcium oxide.

In one aspect, the pharmaceutically-acceptable compound of calcium is present in an amount of from about 10.00 weight percent to about 35.00 weight percent of the composition, or about 10.00 weight percent, about 15.00 weight percent, about 20.00 weight percent, about 25.00 weight percent, about 30.00 weight percent, or about 35.00 weight percent, where any value can be a lower and upper endpoint of a range (e.g., about 25.00 weight percent to about 30.00 weight percent). In another aspect, the amount of the pharmaceutically-acceptable compound of calcium present per unit dose is from about 15.00 weight percent to about 25.00 weight percent of the composition, or about 15.0 weight percent, about 17.00 weight percent, about 19.00 weight percent, about 21.00 weight percent, about 23.00 weight percent, or about 25.00 weight percent, where any value can be a lower and upper endpoint of a range (e.g., about 19.00 weight percent to about 21.00 weight percent).

In one aspect, the compositions described herein include an ionic compound of calcium in an amount such that there is 100 mg to 2,500 mg, 100 mg to 2,000 mg, 100 mg to 1,500 mg, 100 mg to 1,000 mg, or 100 mg to 750 mg of calcium per unit dose. For example, calcium citrate tetrahydrate has a molecular weight of 570.49, of which calcium is 21.08%. Thus, in order for the formulation to have 500 mg of calcium per unit dose, there will be approximately 2,372.3 mg of calcium citrate tetrahydrate per unit dose. In another aspect, 250 to 500 mg of calcium is provided per unit dose of the compositions disclosed herein.

Magnesium

In one aspect, the compositions disclosed herein include a pharmaceutically-acceptable compound of magnesium. In a further aspect, magnesium is necessary for the proper functioning of calcium in the body such as, for example, assisting in entry of calcium ions into cells, thus preventing calcification of tissues. In some aspects, magnesium supplementation may support healthy heart function.

In one aspect, magnesium is required for normal bone structure formation and the functioning of several hundred enzymes, especially those with ATP-dependent phosphorylation, protein synthesis, and carbohydrate metabolism. In a further aspect, magnesium in the extracellular matrix is important to electrical potentials in nerve and muscle cells and the transmission of impulses across neuromuscular junctions.

In one aspect, the pharmaceutically-acceptable compound of magnesium is present in an amount of from about 25.00 weight percent to about 40.00 weight percent of the composition, or about 25.00 weight percent, about 27.00 weight percent, about 29.00 weight percent, about 31.00 weight percent, about 33.00 weight percent, about 35.00 weight percent, about 37.00 weight percent, or about 40.00 weight percent, where any value can be a lower and upper endpoint of a range (e.g., about 29.00 weight percent to about 37.00 weight percent). In another aspect, the amount of the pharmaceutically-acceptable compound of magnesium present per unit dose is from about 5.00 weight percent to about 15.00 weight percent of the composition, or about 5.00 weight percent, about 7.00 weight percent, about 9.00 weight percent, about 11.00 weight percent, about 13.00 weight percent, or about 15.00 weight percent, where any value can be a lower and upper endpoint of a range (e.g., about 9.00 weight percent to about 13.00 weight percent).

In one aspect, the magnesium is provided as an ionic compound of magnesium. Examples of such compounds include, but are not limited to, magnesium citrate, magnesium sulfate monohydrate or heptahydrate, magnesium acetate tetrahydrate, magnesium D-gluconate hydrate, magnesium nitrate hexahydrate, or magnesium oxide. In one aspect, the formulations described herein include an ionic compound of magnesium in an amount such that there is 100 mg to 500 mg, 150 mg to 500 mg, 200 mg to 500 mg, 250 mg to 500 mg, or 300 mg to 500 mg of magnesium per unit dose.

Zinc

In one aspect, the compositions disclosed herein include a pharmaceutically-acceptable compound of zinc. In a further aspect, zinc is especially depleted (from 40% to 78%) during dialysis. In some aspects, zinc is anti-inflammatory, anti-depressant, and functions to support the immune system. Handbook of Nonprescription Drugs, 11th edition, 1996, American Pharmaceutical Association. 2215 Constitution Avenue, NW, Washington, DC 20037. Chapter 19, Nutritional Products, page 388.

In another aspect, zinc is integral to the function of many metalloenzymes and is a cofactor in the synthesis of nucleic acids. In a further aspect, zinc is important in the mobilization of vitamin A from the liver and in several reproductive system hormones and functions in both men and women.

In one aspect, the pharmaceutically-acceptable compound of zinc is present in an amount of from about 0.10 weight percent to about 1.00 weight percent of the composition, about 0.10 weight percent, about 0.20 weight percent, about 0.30 weight percent about, 0.40 weight percent, about 0.50 weight percent, about 0.60 weight percent, about 0.70 weight percent, about 0.80 weight percent, about 0.90 weight percent, or about 1.00 weight percent, where any value can be a lower and upper endpoint of a range (e.g., about 0.40 weight percent to about 0.60 weight percent). In another aspect, the amount of pharmaceutically-acceptable compound of zinc present per unit dose is from about 1.0 weight percent to about 5.00 weight percent of the composition, or about 1.0 weight percent, about 1.5 weight percent, about 2.0 weight percent, about 2.5 weight percent, about 3.0 weight percent, about 3.5 weight percent, about 4.0 weight percent, about 4.5 weight percent, or about 5.0 weight percent, where any value can be a lower and upper endpoint of a range (e.g., about 3.0 weight percent to about 3.5 weight percent).

In one aspect, the zinc is provided as an ionic compound of zinc. Examples of such compounds include, but are not limited to, zinc citrate, zinc citrate dihydrate, zinc acetate dihydrate, or zinc nitrate hexahydrate. In one aspect, the formulations described herein include an ionic compound of zinc in an amount such that there is 1 mg to 40 mg, 1 mg to 30 mg, 1 mg to 20 mg, or 5 mg to 20 mg of zinc per unit dose.

Selenium

In one aspect, the compositions disclosed herein include a pharmaceutically-acceptable compound of selenium. In a further aspect, selenium is highly concentrated in the liver and kidneys and is thus especially depleted during dialysis. In a still further aspect, selenium is a powerful antioxidant and is especially useful when employed against the damaging effects of free radicals. In another aspect, selenium supplementation may protect against hardening of the arteries and harmful molecules. Handbook of Nonprescription Drugs, 11th edition, 1996, American Pharmaceutical Association. 2215 Constitution Avenue, NW, Washington, DC 20037. Chapter 19, Nutritional Products, page 387.

In one aspect, the pharmaceutically-acceptable compound of selenium is present in an amount of from about 0.01 weight percent to about 0.20 weight percent of the composition, or about 0.01 weight percent, about 0.02 weight percent, about 0.04 weight percent, about 0.06 weight percent, about 0.08 weight percent, about 0.10 weight percent, about 0.12 weight percent, about 0.14 weight percent, about 0.16 weight percent, about 0.18 weight percent, or about 0.20 weight percent, where any value can be a lower and upper endpoint of a range (e.g., about 0.06 weight percent to about 0.08 weight percent). In another aspect, the amount of the pharmaceutically-acceptable compound of selenium present per unit dose is from about 0.10 weight percent to about 2.00 weight percent of the composition, or about 0.10 weight percent, about 0.25 weight percent, about 0.50 weight percent, about 0.75 weight percent, about 1.00 weight percent, about 1.25 weight percent, about 1.50 weight percent, about 1.75 weight percent, or about 2.00 weight percent, where any value can be a lower and upper endpoint of a range (e.g., about 0.50 weight percent to about 1.00 weight percent).

In one aspect, the selenium is provided as an ionic compound of selenium such as, for example, sodium selenate, sodium selenite, L-selenomethionine, or a combination thereof. In one aspect, the formulations described herein include an ionic compound of selenium in an amount such that there is 10 μg to 400 μg, 10 μg to 300 μg, 10 μg to 200 μg, 10 μg to 100 μg, or 25 μg to 80 μg of selenium per unit dose.

Iron

In one aspect, the compositions disclosed herein include a pharmaceutically-acceptable compound of iron. In a further aspect, iron is vital in preventing anemia. Handbook of Nonprescription Drugs, 11$^{th}$ edition, 1996, American Pharmaceutical Association. 2215 Constitution Avenue, NW, Washington, DC 20037. Chapter 19, Nutritional Products, page 380. In still another aspect, biochemically, iron is important to oxygen and electron transport as well as prevent anemia and improve the quality and quantity of red blood cells. In a further aspect, heme iron is found in meats and is well-absorbed, while non-heme iron is poorly absorbed. In a still further aspect, supplementation of iron may be particularly important for patients consuming diets that include little or no meat.

In one aspect, the pharmaceutically-acceptable compound of iron is present in an amount of from about 0.10 weight percent to about 3.00 weight percent of the composition, about 0.10 weight percent, about 0.50 weight percent, about 1.00 weight percent, about 1.50 weight percent, about 2.00 weight percent, about 2.50 weight percent, or about 3.00 weight percent, where any value can be a lower and upper endpoint of a range (e.g., about 1.50 weight percent to about 2.00 weight percent). In another aspect, the amount of pharmaceutically-acceptable compound of zinc present per unit dose is from about 5.00 weight percent to about 20.00 weight percent of the composition, or about 5.00 weight percent, about 7.5 weight percent, about 10.00 weight percent, about 12.50 weight percent, about 15.00 weight percent, about 17.50 weight percent, or about 20.00 weight percent, where any value can be a lower and upper endpoint of a range (e.g., about 7.50 weight percent to about 12.50 weight percent).

In one aspect, the iron is provided as an ionic compound of iron such as, for example, iron gluconate, iron gluconate dihydrate, or iron sulfate heptahydrate. In one aspect, the formulations described herein include an ionic compound of iron in an amount such that there is 1 mg to 45 mg, 1 mg to 30 mg, 1 mg to 20 mg, or 5 mg to 20 mg of iron per unit dose.

Manganese

In one aspect, the compositions disclosed herein include a pharmaceutically-acceptable compound of manganese. Manganese helps the body break down fats, carbohydrates, and proteins. For example, manganese can work in conjunction with or activate specific enzymes. Manganese deficiency can result in abnormal metabolism of carbohydrates or fats.

In one aspect, the pharmaceutically-acceptable compound of manganese is present in an amount of from about 0.01 weight percent to about 0.20 weight percent of the composition, or about 0.01 weight percent, about 0.02 weight percent, about 0.04 weight percent, about 0.06 weight percent, about 0.08 weight percent, about 0.10 weight percent, about 0.12 weight percent, about 0.14 weight percent, about 0.16 weight percent, about 0.18 weight percent, or about 0.20 weight percent, where any value can be a lower and upper endpoint of a range (e.g., about 0.08 weight percent to about 0.12 weight percent). In another aspect, the amount of the pharmaceutically-acceptable compound of manganese present per unit dose is from about 0.10 weight percent to about 1.00 weight percent of the composition, or about 0.10 weight percent, about 0.20 weight percent, about 0.30 weight percent, about 0.40 weight percent, about 0.50 weight percent, about 0.60 weight percent, about 0.70 weight percent, about 0.80 weight percent, about 0.90 weight percent, or about 1.00 weight percent, where any value can be a lower and upper endpoint of a range (e.g., about 0.50 weight percent to about 0.70 weight percent).

In one aspect, the iron is provided as an ionic compound of manganese such as, for example, manganese citrate, manganese gluconate, or manganese chloride. In one aspect, the formulations described herein include an ionic compound of manganese in an amount such that there is 0.1 mg to 10 mg, 0.1 mg to 5 mg, 0.5 mg to 5 mg, or 1 mg to 3 mg of manganese per unit dose.

Chromium

In one aspect, the compositions disclosed herein include a pharmaceutically-acceptable compound of chromium. Chromium plays a role in how the body breaks down fats and carbohydrates. Chromium can help control blood sugar levels, lower cholesterol levels, and help with weight loss.

In one aspect, the pharmaceutically-acceptable compound of chromium is present in an amount of from about 0.001 weight percent to about 0.10 weight percent of the composition, or about 0.001 weight percent, about 0.005 weight percent, about 0.010 weight percent, about 0.020 weight percent, about 0.030 weight percent, about 0.040 weight percent, about 0.050 weight percent, about 0.060 weight percent, about 0.070 weight percent, about 0.080 weight percent, about 0.090 weight percent, or about 0.10 weight percent, where any value can be a lower and upper endpoint of a range (e.g., about 0.0030 weight percent to about 0.005 weight percent). In another aspect, the amount of the pharmaceutically-acceptable compound of chromium present per unit dose is from about 0.001 weight percent to about 0.10 weight percent of the composition, or about 0.001 weight percent, about 0.005 weight percent, about 0.010 weight percent, about 0.020 weight percent, about 0.030 weight percent, about 0.040 weight percent, about 0.050 weight percent, about 0.060 weight percent, about 0.070 weight percent, about 0.080 weight percent, about 0.090 weight percent, or about 0.10 weight percent, where any value can be a lower and upper endpoint of a range (e.g., about 0.020 weight percent to about 0.030 weight percent).

In one aspect, the chromium is provided as an ionic compound of chromium such as, for example, chromium picolinate. In one aspect, the formulations described herein include an ionic compound of chromium in an amount such that there is 0.1 μg to 10 μg, 0.1 μg to 5 μg, 0.5 μg to 5 μg, or 1 μg to 3 μg of chromium per unit dose.

Copper

In one aspect, the compositions disclosed herein include a pharmaceutically-acceptable compound of copper. In certain aspects, copper can affect the production of certain hormones and enzymes in the body that are responsible for the maintenance of vital bodily functions.

In one aspect, the pharmaceutically-acceptable compound of copper is present in an amount of from about 0.01 weight percent to about 0.50 weight percent of the composition, or about 0.01 weight percent, about 0.05 weight percent, about 0.10 weight percent, about 0.15 weight percent, about 0.20 weight percent, about 0.25 weight percent, about 0.30 weight percent, about 0.35 weight percent, about 0.40 weight percent, about 0.45 weight percent, or about 0.50 weight percent, where any value can be a lower and upper endpoint of a range (e.g., about 0.10 weight percent to about 0.20 weight percent). In another aspect, the amount of the pharmaceutically-acceptable compound of copper present per unit dose is from about 0.10 weight percent to about 2.00 weight percent of the composition, or about 0.10 weight percent, about 0.20 weight percent, about 0.30 weight percent, about 0.40 weight percent, about 0.50 weight percent, about 0.60 weight percent, about 0.70 weight percent, about 0.80 weight percent, about 0.90 weight percent, about 1.00 weight percent, about 1.00 weight percent, about 1.10 weight percent, about 1.20 weight percent, about 1.30 weight percent, about 1.40 weight percent, about 1.50 weight percent, about 1.60 weight percent, about 1.70 weight percent, about 1.80 weight percent, about 1.90 weight percent, or about 2.00 weight percent, where any value can be a lower and upper endpoint of a range (e.g., about 0.80 weight percent to about 1.20 weight percent).

In one aspect, the copper is provided as an ionic compound of copper such as, for example, copper gluconate. In one aspect, the formulations described herein include an ionic compound of copper in an amount such that there is 0.1 mg to 10 mg, 0.1 mg to 5 mg, 0.5 mg to 5 mg, or 1 mg to 3 mg of chromium per unit dose.

L-Carnitine

L-carnitine is a vitamin-like molecule that is used by the body to transport fatty acids into the mitochondria for breakdown. It is a non-proteinogenic amino acid that is synthesized in the liver and kidneys from lysine and methionine. This essential amino acid is completely or almost completely depleted from the blood with chronic kidney dialysis. L-carnitine deficiency has been linked to adverse cardiac conditions including, but not limited to, arrhythmias and angina; thus, in one aspect, supplementing with L-carnitine can reduce the incidence of cardiac damage and cardiac events associated with kidney dialysis. In a further aspect, L-carnitine deficiency has been shown to limit mitochondrial fat metabolism in the heart and other organs; in this aspect, supplementation with L-carnitine may help restore normal mitochondrial fat metabolism. In still another aspect, L-carnitine supplementation can provide support in cases of muscle weakness and may protect against circulatory disorders. In a still further aspect, L-carnitine has been shown to be important in oxidation of fatty acids and cellular energy management.

In one aspect, the compositions disclosed herein include a pharmaceutically-acceptable compound of L-carnitine. Examples of pharmaceutically-acceptable compounds of L-carnitine include, but are not limited to, acetyl-L-carnitine or L-carnitine-L-tartrate, which can be metabolized in the blood by plasma esterases to produce L-carnitine. In other aspects, L-carnitine can be used directly.

In one aspect, the pharmaceutically-acceptable compound of L-carnitine is present in an amount of from about 20.00 weight percent to about 30.00 weight percent of the composition, or about 20.00 weight percent, about 21.00 weight percent, about 22.00 weight percent, about 23.00 weight percent, about 24.00 weight percent, about 25.00 weight percent, about 26.00 weight percent, about 27.00 weight percent, about 28.00 weight percent, about 29.00 weight percent, or about 30.00 weight percent, where any value can be a lower and upper endpoint of a range (e.g., about 24.00 weight percent to about 26.00 weight percent). In another aspect, the amount of the pharmaceutically-acceptable compound of L-carnitine present per unit dose is from about 10.00 weight percent to about 25.00 weight percent of the composition, or about 10.00 weight percent, about 12.00 weight percent, about 14.00 weight percent, about 16.00 weight percent, about 18.00 weight percent, about 20.00 weight percent, about 22.00 weight percent, or about 25.00 weight percent, where any value can be a lower and upper endpoint of a range (e.g., about 14.00 weight percent to about 18.00 weight percent).

In one aspect, the amount of the pharmaceutically-acceptable compound of L-carnitine present per unit dose is from 100 mg to 3,500 mg, 500 mg to 2,500 mg, 500 mg to 1,000 mg, 1,000 mg to 2,000 mg of L-carnitine per unit dose. For example, 2,239 mg of L-carnitine-L-tartrate will provide 1,500 mg of L-carnitine per unit dose. In a further aspect, 500 mg to 2,500 mg of acetyl-L-carnitine or L-carnitine-L-tartrate is included in the compositions disclosed herein.

Glutathione

In one aspect, the compositions disclosed herein include glutathione or a pharmaceutically-acceptable salt thereof. Glutathione is composed of the amino acids glycine, cysteine, and glutamic acid. It is produced by the liver and involved in many body processes. Glutathione is involved in tissue building and repair, making chemicals and proteins needed in the body, and in immune system function. Glutathione provides several health benefits related to aging, alcohol use disorder, liver disease, heart disease, and many other conditions. Glutathione as used herein also includes the reduced or oxidized forms of glutathione.

In one aspect, glutathione or a pharmaceutically-acceptable salt thereof is present in an amount of from about 1.00 weight percent to about 5.00 weight percent of the composition, or about 1.00 weight percent, about 1.50 weight percent, about 2.00 weight percent, about 2.50 weight percent, about 3.00 weight percent, about 3.50 weight percent, about 4.00 weight percent, about 4.50 weight percent, or about 5.00 weight percent, where any value can be a lower and upper endpoint of a range (e.g., about 1.5 weight percent to about 2.5 weight percent). In another aspect, the amount of glutathione or the pharmaceutically-acceptable salt thereof present per unit dose is from about 5.00 weight percent to about 20.00 weight percent of the composition, or about 5.00 weight percent, about 7.00 weight percent, about 9.00 weight percent, about 11.00 weight percent, about 13.00 weight percent, about 15.00 weight percent, about 17.00 weight percent, or about 20.00 weight percent, where any value can be a lower and upper endpoint of a range (e.g., about 11.00 weight percent to about 15.00 weight percent).

In one aspect, the amount of glutathione or a pharmaceutically-acceptable salt thereof per unit dose is from 1 mg to 500 mg, 50 mg to 300 mg, or 100 mg to 250 mg.

In another aspect, the compositions disclosed herein incorporate one or more amino acids. In a further aspect, these amino acids can be proteinogenic or non-proteinogenic. In one aspect, glutathione is L-glutathione. In another aspect, glutathione is reduced L-glutathione (CAS no. 200-725-4).

L-Arginine

In one aspect, the compositions disclosed herein include L-arginine or a pharmaceutically-acceptable salt thereof. L-Arginine provides the body with ingredients that it needs to increase nitric oxide production in the body, which helps relax and dilate blood vessels and improve circulation and protects against heart disease. In one aspect, L-arginine is present in the compositions disclosed herein in an amount of from about 1.00 weight percent to about 10.00 weight percent of the composition, or about 1.00 weight percent, about 2.00 weight percent, about 3.00 weight percent, about 4.00 weight percent, about 5.00 weight percent, about 6.00 weight percent, about 7.00 weight percent, about 8.00 weight percent, about 9.00 weight percent, or about 10.00 weight percent, where any value can be a lower and upper endpoint of a range (e.g., about 4.00 weight percent to about 5.00 weight percent).

In one aspect, the amount of L-arginine present per unit dose is from 50 mg to 1,000 mg, 50 mg to 750 mg, 100 mg to 500 mg, or 300 mg to 500 mg.

L-Citrulline

In one aspect, the compositions disclosed herein include L-citrulline or a pharmaceutically-acceptable salt thereof. L-Citrulline is effective at maintaining elevated arginine levels for long periods of time. L-Citrulline is more bio-available and it is converted to L-arginine in the kidneys. In one aspect, L-citrulline is present in the compositions disclosed herein in an amount of from about 1.00 weight percent to about 10.00 weight percent of the composition, or about 1.00 weight percent, about 2.00 weight percent, about 3.00 weight percent, about 4.00 weight percent, about 5.00 weight percent, about 6.00 weight percent, about 7.00 weight percent, about 8.00 weight percent, about 9.00 weight percent, or about 10.00 weight percent, where any value can be a lower and upper endpoint of a range (e.g., about 4.00 weight percent to about 5.00 weight percent).

In one aspect, the amount of L-citrulline present per unit dose is from 50 mg to 1,000 mg, 50 mg to 750 mg, 100 mg to 500 mg, or 300 mg to 500 mg.

Red Beetroot Extract

In one aspect, the compositions disclosed herein include red beetroot extract. Red beetroot extract can reduce total cholesterol, especially LDL cholesterol and triglycerides in people with heart disease and high blood pressure. Furthermore, red beets provide nitrates that get converted to nitric oxide as well as fiber and other plant-based polyphenol antioxidants. Red beetroot extract can improve heart, brain, and immune health while providing healthy levels of energy on a daily basis.

In one aspect, red beetroot extract is present in the compositions disclosed herein in an amount of from about 1.00 weight percent to about 15.00 weight percent of the composition, or about 1.00 weight percent, about 2.00 weight percent, about 3.00 weight percent, about 4.00 weight percent, about 5.00 weight percent, about 6.00 weight percent, about 7.00 weight percent, about 8.00 weight percent, about 9.00 weight percent, about 10.00 weight percent, about 11.00 weight percent, about 12.00 weight percent, about 13.00 weight percent, about 14.00 weight percent, or about 15.00 weight percent, where any value can be a lower and upper endpoint of a range (e.g., about 7.00 weight percent to about 8.00 weight percent).

In one aspect, the amount of red beetroot extract present per unit dose is from 50 mg to 1,000 mg, 50 mg to 850 mg, 100 mg to 800 mg, or 500 mg to 800 mg.

Alpha Lipoic Acid

In one aspect, the compositions disclosed herein include alpha lipoic acid (ALA). Alpha lipoic acid enhances the body's ability to use its own insulin to lower blood sugar in people with type II diabetes and may help reduce the symptoms of peripheral neuropathy, which is nerve damage caused by diabetes. In one aspect, alpha lipoic acid is present in the compositions disclosed herein in an amount of from about 1.00 weight percent to about 10.00 weight percent of the composition, or about 1.00 weight percent, about 2.00 weight percent, about 3.00 weight percent, about 4.00 weight percent, about 5.00 weight percent, about 6.00 weight percent, about 7.00 weight percent, about 8.00 weight percent, about 9.00 weight percent, or about 10.00 weight percent, where any value can be a lower and upper endpoint of a range (e.g., about 3.00 weight percent to about 4.00 weight percent).

In one aspect, the amount of alpha lipoic acid present per unit dose is from 50 mg to 1,000 mg, 50 mg to 500 mg, 100 mg to 500 mg, or 200 mg to 400 mg.

Boron

In one aspect, the compositions disclosed herein include a pharmaceutically-acceptable compound of boron. Boron is present in red onions and garlic. Boron is excellent for producing hormones such as testosterone, cortisone, and estrogen. Boron also improves the human system against bacterial and fungal infections. In one aspect, the boron is provided as an ionic compound of boron. Examples of such compounds include, but are not limited to, boroglycinate and sodium tetraborate.

In one aspect, the pharmaceutically-acceptable compound of boron is present in an amount of from about 0.001 weight percent to about 0.05 weight percent of the composition, or about 0.001 weight percent, about 0.005 weight percent, about 0.010 weight percent, about 0.105 weight percent, about 0.020 weight percent, about 0.025 weight percent, about 0.030 weight percent, about 0.035 weight percent, about 0.040 weight percent, about 0.045 weight percent, or about 0.050 weight percent, where any value can be a lower and upper endpoint of a range (e.g., about 0.005 weight percent to about 0.020 weight percent).

In one aspect, the amount of the pharmaceutically-acceptable compound of boron present per unit dose is from 0.10 mg to 5.0 mg, 0.5 mg to 3.0 mg, 1.0 mg to 3.0 mg, or 1.0 mg to 2.0 mg.

Apple Pectin

Apple pectin is a water-soluble fiber, which has a gel-forming effect when mixed with water. Apple pectin is a rich source of soluble fiber, which plays an important role in the prevention and treatment of disease. Apple pectin has numerous health benefits including, but not limited to, a reduction in blood sugar levels, total cholesterol levels, triglyceride levels and weight. A reduction in one or all of these factors will contribute to a reduction in high blood pressure as well. Apple pectin can also improve intestinal environment.

In one aspect, apple pectin is present in the compositions disclosed herein in an amount of from about 1.00 weight percent to about 10.00 weight percent of the composition, or about 1.00 weight percent, about 2.00 weight percent, about 3.00 weight percent, about 4.00 weight percent, about 5.00 weight percent, about 6.00 weight percent, about 7.00 weight percent, about 8.00 weight percent, about 9.00 weight percent, or about 10.00 weight percent, where any value can be a lower and upper endpoint of a range (e.g., about 5.00 weight percent to about 7.00 weight percent).

In one aspect, the amount of apple pectin present per unit dose is from 50 mg to 3,500 mg, 50 mg to 2,000 mg, 100 mg to 1,000 mg, or 200 mg to 800 mg.

Sugar Beet Pectin

Sugar beet pectin is a byproduct of sugar extraction from sugar beets. Its good emulsifying properties stem from its complex macromolecular structure, i.e. a polysaccharide covalently linked to a protein. Compared to apple or citrus pectin. SBP is non-gelling due to higher acetylation of the hydroxyls at C2 and C3, and has a higher content of ferulic acid, which is attached to arabinans and arabinogalactans in the RGI region. Sugar beet pectin has numerous health benefits including, but not limited to, a reduction of post-prandial glycemic response and a positive effect on the blood cholesterol level.

In one aspect, sugar beet pectin is present in the compositions disclosed herein in an amount of from about 0.50 weight percent to about 5.00 weight percent of the composition, or about 0.50 weight percent, about 1.00 weight percent, about 1.50 weight percent, about 2.00 weight percent, about 2.50 weight percent, about 3.00 weight percent, about 3.50 weight percent, about 4.00 weight percent, about 4.50 weight percent, or about 5.00 weight percent, where any value can be a lower and upper endpoint of a range (e.g., about 1.00 weight percent to about 3.50 weight percent).

In one aspect, the amount of sugar beet pectin present per unit dose is from 5 mg to 1,000 mg, 5 mg to 500 mg, 50 mg to 300 mg, or 200 mg to 300 mg.

Citrus Bioflavonoids

In one aspect, the compositions disclosed herein include citrus bioflavonoids. In a further aspect, citrus fruits are excellent sources of vitamin C and citrus bioflavonoid preparations sourced from whole citrus fruits or citrus rinds/peels or pith may be rich in vitamin C. In a further aspect, the citrus bioflavonoids can be from lemons, limes, grapefruits, oranges, tangerines, or a combination thereof. In a further aspect, the citrus bioflavonoids can include rutin, quercetin, tangeritin, diosmetin, diosmin, naringin, nairrutin, neohesperidin, nobiletin, hesperidin, and combinations thereof.

In a still further aspect, citrus bioflavonoids may be anti-inflammatory, antioxidant, or anti-microbial. In still another aspect, citrus bioflavonoids may improve capillary permeability and circulation, hypertension, swelling or edema, and insulin response, or a combination thereof. In still another aspect, sources of citrus bioflavonoids may contain flavor compounds that render the compositions disclosed herein more palatable. In one aspect, the citrus bioflavonoid can be present in water at a concentration of from about 25 wt %/v to about 99 wt %/v.

Powdered Extract of Cranberry and Cherry

In one aspect, the compositions disclosed herein include powdered extracts of cranberry and cherry. In another aspect, cranberry and cherry extracts may contain flavor compounds that render the compositions disclosed herein more palatable. In a further aspect, cranberry and cherry extracts are high in antioxidants, vitamins, and minerals.

In a still further aspect, cranberry extract contains D-mannose, a sugar that has anti-biofilm (bacterial biofilm that is) properties, binds to and agglomerates bacteria in the urinary tract, thus helping to prevent urinary tract infections, which can be especially important for dialysis patients.

In one aspect, the cherry extract is from tart cherry. Further in this aspect, consumption of tart cherry extract may reduce side effects of statins, may improve blood cholesterol levels, may reduce inflammation related to arthritis and/or obesity, and may support a healthy metabolism.

In one aspect, some minerals are not to be included in the compositions disclosed herein.

Potassium

In one aspect, potassium is excluded from the compositions described herein. In some aspects, high potassium levels can cause muscle and heart problems. In a further aspect, potassium levels can rise between dialysis sessions and may affect the heartbeat.

Sodium

In another aspect, the compositions disclosed herein exclude sodium. In one aspect, increased sodium consumption causes thirst and may lead to water retention. In a further aspect, excess sodium consumption and/or high sodium levels can raise the blood pressure.

Phosphorus

In one aspect, the compositions disclosed herein exclude phosphorus. In a further aspect, too much phosphorus in the blood can cause calcium resorption from the bones.

In still another aspect, too much phosphorus can cause the skin to itch. Handbook of Nonprescription Drugs, $11^{th}$ edition, 1996, American Pharmaceutical Association. 2215 Constitution Avenue, NW, Washington, DC 20037. Chapter 19, Nutritional Products, page 383-384. In one aspect, a phosphate binder is provided to the patient alongside the formulations disclosed herein.

The compositions described herein can be formulated using techniques known in the art. In one aspect, the minerals, vitamins, and amino acids supplied in dry form are admixed with one another to produce a dry powder. In addition to the minerals, vitamins, and amino acids, other pharmaceutically-acceptable fillers can be added to formulate the supplement in powder form. For example, polysaccharides such as, for example, maltodextrin, can be used to formulate the compositions described herein.

The compositions described herein are intended to be taken orally. In one aspect, the compositions described herein can be formulated as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In one aspect, the unit dose composition includes from about 200 mg to about 800 mg of the composition described herein, or about 200 mg, about 300 mg, about 400 mg, about 500 mg, about 600 mg, about 700 mg, or about 800 mg, about 100 mg, where any value can be a lower and upper endpoint of a range (e.g., about 400 mg to about 600 mg).

In other aspects, the compositions can be formulated as a powder that can be mixed with water or another beverage. Alternatively, the powder form of the composition can be admixed with food such as yogurt, peanut butter, or other foods that readily mix with the compositions.

Kits

One or more additional components can be taken with the compositions described herein. In one aspect, an omega 3 fatty acid can be taken with the compositions described herein. Omega 3 fatty acids are lipid soluble macronutrients that are important to metabolism (i.e., energy production captured in the form of ATP). Omega 3 fatty acids are partially removed from the body with chronic kidney dialysis. Omega 3 fatty acids have been shown to reduce inflammation and thus to lower the risk of chronic diseases (including heart disease). They are believed to be important for cognitive function and also have been shown to reduce triglycerides while increasing high-density lipoproteins (HDL) cholesterol. Omega 3 fatty acids have been linked to improvement in a number of other conditions including from skin, joint, eye, and gastrointestinal conditions. In one aspect, supplementation with omega 3 fatty acids can be especially important for improving blood pressure, blood circulation, and blood vessel elasticity while preventing cardiovascular and coronary events in persons with high cardiovascular risk. Marine Omega 3 Fatty Acids: https://en.wikipedia.org/wiki/Fatty_acid_metabolism Omega 3 fatty acids are found in fish, some plants, nut oils, and algae, and are not always consumed in high enough amounts through the standard diet. In one aspect, it is important to replenish the body's supply of omega 3 fatty acids, since these important macronutrients cannot be synthesized by the body. In another aspect, marine omega 3 fatty acids (i.e., from fish or algae) have preferable amounts of DHA (docosahexaenoic acid) and EPA (eicosapentaenoic acid) as compared to omega 3 fatty acids from plant sources, which primarily contain ALA (alpha linolenic acid), a compound that is not efficiently utilized by the body.

In still another aspect, the formulations disclosed herein include marine omega 3 fatty acids. In a further aspect, the marine omega 3 fatty acids can be sourced from salmon, mackerel, sardines, tuna, or herring. Many Western diets incorporate higher dietary omega 6 fatty acids, which can promote inflammation. In another aspect, it is important to supplement omega 3 fatty acids, especially in hemodialysis patients, to reduce inflammation and the risk of death. In another aspect, the amount of Omega 3 is significantly higher than the amount Omega 6.

In yet another aspect, hemodialysis is believed to upregulate oxidative mechanisms, which could lead to peroxidation of omega 3 fatty acids; this, in turn, can lead to breakdown of the fatty acid structure and loss of function. In this aspect, supplementation with omega 3 fatty acids can be used to replenish the supply of nutrients destroyed by peroxidation.

In one aspect, the marine omega 3 fatty acids are provided as wild Alaskan salmon oil or marine algal oil. In a further aspect, the EPA:DHA ratio of the marine omega 3 fatty acids is from 1:1 to 4:1. In one aspect, the amount of marine omega 3 fatty acids present per unit dose is from 500 mg to 4,000 mg, 500 mg to 3,000 mg, 500 mg to 2,000 mg, or 500 mg to 1,500 mg. In another aspect, 1000 mg of marine omega 3 fatty acids are provided per unit dose of the compositions disclosed herein.

In another aspect, coenzyme $Q_{10}$ ($CoQ_{10}$) can be taken with the compositions described herein. $CoQ_{10}$ acts as an antioxidant and protects the cell membrane against oxidative stress. In another aspect, $CoQ_{10}$ is an important coenzyme in the mitochondria (and other parts of the cell) and participates in cellular respiration, which ultimately generates energy in the form of adenosine triphosphate. In still another aspect, $CoQ_{10}$ protects against low-density lipoproteins (LDL) oxidation, which is vital for heart health. In a further aspect, reduced form of $CoQ_{10}$ ($CoQ_{10}H_2$) can regenerate vitamin E from the alpha-tocopheroxyl radical, thus leading to a reduction of oxidative stress.

In one aspect, certain patients require intake of $CoQ_{10}$ that is higher than provided by the average diet. These include, but are not limited to, athletes, patients with hyperthyroidism, patients who are taking statins, and the elderly. Thus, in one aspect, elderly dialysis patients may especially benefit from $CoQ_{10}$ supplementation. In a related aspect, $CoQ_{10}$ can decrease insulin requirements in patients with diabetes; thus, diabetic dialysis patients may also benefit from $CoQ_{10}$ supplementation.

In another aspect, however, $CoQ_{10}$ supplementation should be avoided in patients taking warfarin or other blood thinners, as it can reduce the activity of these medications. In this aspect, the compositions disclosed herein do not include $CoQ_{10}$.

In one aspect, $CoQ_{10}$ in the compositions disclosed herein is provided as ubiquinol, a reduced form of $CoQ_{10}$ that has a particularly high uptake percentage and subsequently leads to an increase of $CoQ_{10}$ levels in the blood. Ubiquinol effectively regenerates vitamin E from alpha-tocopherol radical. In one aspect, the amount of $CoQ_{10}H_2$ (e.g., ubiquinol) present per unit dose is from 70 mg to 400 mg, 70 mg to 300 mg, or 150 mg to 250 mg. In another aspect, 200 mg of ubiquinol are included in the compositions disclosed herein.

In one aspect, turmeric can be taken with the compositions described herein. Turmeric has anti-inflammatory and antioxidant properties that are in some aspects useful to the kidneys. In another aspect, the formulations disclosed herein do not include turmeric. In some aspects, turmeric should not be given to patients who are sensitive or allergic, pregnant or nursing, diabetic and taking blood thinners, patients with gall bladder conditions, and/or patients with digestive system disorders such as GERD (gastroesophageal reflux disease). In one aspect, turmeric is prepared in a separate distribution form (e.g., a separate capsule) and given to patients at their healthcare providers' discretion. In still another aspect, turmeric is provided with the compositions described herein unless the patient is going to undergo surgery and/or has a bleeding disorder, since turmeric is known to be a powerful blood thinner.

In one aspect, piperine can be taken with the compositions described herein. In some aspects, turmeric is not easily absorbed by the body and piperine enhances absorption by 10 to 20 fold. In one aspect, the formulations disclosed herein include 100 mg of piperine for every 500 mg of turmeric. In one aspect, the amount of turmeric present per unit dose is from 1 g to 3 g, 1.5 g to 2.5 g, or 2 g.

In one aspect, the compositions described herein is part of a kit, where one compartment or vial has a mixture of the composition described herein in dry form (e.g., tablet, powder), and a second compartment containing other components (e.g., marine omega 3 fatty acids in capsule form, ubiquinol in gel form, turmeric is in a capsule, or any combination thereof).

Methods of Use

The compositions described herein have numerous health applications and can provide relief and quality of life to a subject. In one aspect, the compositions described herein can treat a subject with type I diabetes or type II diabetes. In another aspect, the compositions described herein can treat a subject diagnosed with prediabetes. Diabetes can strike anyone, from any walk of life. Diabetes is one of the most widespread diseases. Worldwide, more than 537 million people have diabetes, and more than 34 million Americans have been diagnosed with diabetes. Diabetes is a serious condition that causes higher than normal blood sugar levels. Diabetes occurs when your body cannot make or effectively use its own insulin, a hormone made by special cells in the pancreas called islets. Insulin serves as a "key" to open the cells, to allow the sugar (glucose) from the food to enter the cells. The body uses that glucose for energy.

Type 1 and type 2 diabetes are the most common forms of the disease, but there are also other kinds, such as gestational diabetes, which occurs during pregnancy, as well as other forms. In one aspect, the compositions reduce or prevent one or more symptoms of type I diabetes or type II diabetes when compared to the same subject prior to the administration of the composition. Examples of such symptoms include, but are not limited to, weight loss, polydipsia, polyuria, polyphagia, blurred vision, headache, fatigue, slow healing of cuts, itchy skin, or any combination thereof. In another aspect, the methods described herein reduce the amount of insulin required by the subject having type II diabetes.

In another aspect, the compositions described herein can improve the health of a subject undergoing dialysis. One in ten persons around the world has some degree of kidney disease and, in America, one in three adults is at risk of kidney disease. More than 4.5 million persons worldwide are suffering from kidney failure. By the time a patient has lost 85%-90% of their kidneys' function—a situation called end-stage kidney disease—the patient must get a kidney transplant or be treated on dialysis. Kidney dialysis helps keep the body in balance by (1) removing toxic waste such as urine, salt, and excess water, and (2) control blood pressure.

In one aspect, the compositions described herein are to be administered to patients with kidney disease and/or undergoing kidney dialysis, or individuals at risk of kidney diseases (lifestyle, family history, etc.). The amount of composition administered to the patient should not exceed the recommended daily dose for each component. The compositions can be administered to the patient prior to dialysis, during dialysis, after dialysis, and any combination thereof. The nutritional supplement described herein is designed to support kidney and cardiac function as well as mitochondrial energy function needs in patients undergoing hemodialysis. This supplement replenishes essential vitamins and minerals that are lost during dialysis, does not contain compounds that may specifically cause harm to dialysis patients, and provides support for tissues undergoing oxidative stress. By replenishing the minerals and vitamins lost during dialysis, the subject will have increased energy levels that will permit the subject to lead a more productive life.

In one aspect, the compositions described herein can replenish essential vitamins and minerals that are lost during kidney dialysis, such as, for example, hemodialysis or peritoneal dialysis. In another aspect, the patient has a kidney disease or a kidney transplant. In one aspect, the compositions described herein provide one or more benefits after dialysis when compared to the same subject prior to the administration of the composition: improved recovery after dialysis treatment, increased body strength, improved appetite, improved sleep, reduced pain in the body preferably in joints.

In another aspect, the compositions described herein can enhance one or more physical properties of a subject after exercise. Athletes, whether professional or amateurs, are many times exposing themselves to practices that are on the 'edge' for what their bodies can tolerate. It is not uncommon for them in such period having a less efficient immune system defense and are seeking ways by supplement intake to support their bodies during such frenzy activities. It is also important that they have the energy level to go through these hard periods of extreme exercises. In one aspect, the compositions described herein can improve recovery after exercise, increase energy, increase body strength, improve appetite, improved sleep, reduce muscle and joint pain, or any combination thereof.

In another aspect, the compositions described herein can treat myalgic encephalomyelitis in a subject. Myalgic encephalomyelitis, also called chronic fatigue syndrome or ME/CFS, is a long-term condition with a wide range of symptoms. The most common symptom is extreme tiredness. ME/CFS can affect anyone, including children. It is more common in women and tends to develop between mid-20s and mid-40s. The severity of symptoms can vary from day to day, or even within a day. Extreme tiredness and other physical symptoms can make it hard to carry out everyday activities. Patients may have to make some major lifestyle changes. ME/CFS can also affect the mental and emotional health. In one aspect, the compositions described herein can reduce or prevent one or more symptoms of myalgic encephalomyelitis such as, for example, extreme tiredness, difficulty with sleeping, feeling dizzy or sick, sore throat, flu-like symptoms, heart palpitations, muscle or joint pain, headaches, difficulty with thinking, memory and concentration, mental fog and fatigue, and any combination thereof.

In another aspect, the compositions described herein can reduce or prevent one or more symptoms of Crohn's disease in a subject. Crohn's disease is a type of inflammatory bowel disease (IBD). It causes inflammation of your digestive tract, which can lead to abdominal pain, severe diarrhea, fatigue, weight loss and malnutrition. Inflammation caused by Crohn's disease can involve different areas of the digestive tract in different people. This inflammation often spreads into the deeper layers of the bowel. Crohn's disease can be both painful and debilitating, and sometimes may lead to life-threatening complications. In one aspect, the compositions described herein can reduce or prevent one or more symptoms of Crohn's disease such as, for example, diarrhea, fever, fatigue, abdominal pain and cramping, blood in stool, mouth sores, reduced appetite and weight loss, or pain or drainage near or around the anus.

Depending upon the condition to be treated, the amount of the composition described herein can vary. In one aspect, the subject is administered from about 1 gram to about 2 grams of the composition daily. In another aspect, the subject is administered about 1 gram, about 1.2 gram, about 1.4 gram, about 1.6 gram, about 1.8 gram, or about 2 grams of the composition daily, where any value can be a lower and upper endpoint of a range (e.g., about 1.2 to about 1.6 mg).

Aspects

The present disclosure can be described in accordance with the following numbered aspects, which should not be confused with the claims.

Aspect 1. A composition comprising
    (a) vitamin B1
    (b) vitamin B2
    (c) vitamin B3
    (d) vitamin B5
    (e) vitamin B6
    (f) vitamin B7
    (g) vitamin B9
    (h) vitamin B12
    (i) vitamin C
    (j) vitamin $D_3$
    (k) a pharmaceutically-acceptable compound of calcium (l) a pharmaceutically-acceptable compound of magnesium (m) a pharmaceutically-acceptable compound of zinc (n) a pharmaceutically-acceptable compound of selenium (o) a pharmaceutically-acceptable compound of iron (p) a pharmaceutically-acceptable compound of L-carnitine (q) a pharmaceutically-acceptable compound of manganese (r) a pharmaceutically-acceptable compound of chromium(s)

(s) a pharmaceutically-acceptable compound of copper (t) glutathione or pharmaceutically-acceptable salt thereof.

Aspect 2. The composition of Aspect 1, wherein the composition comprises (a) vitamin B1 in an amount of from about 0.10 weight percent to about 0.50 weight percent of the composition;

(b) vitamin B2 in an amount of from about 0.10 weight percent to about 0.50 weight percent of the composition;

(c) vitamin B3 in an amount of from about 0.10 weight percent to about 0.50 weight percent of the composition;

(d) vitamin B5 in an amount of from about 0.01 weight percent to about 0.50 weight percent of the composition;

(e) vitamin B6 in an amount of from about 0.01 weight percent to about 0.50 weight percent of the composition;

(f) vitamin B7 in an amount of from about 0.10 weight percent to about 1.00 weight percent of the composition;

(g) vitamin B9 in an amount of from about 0.001 weight percent to about 0.10 weight percent of the composition;

(h) vitamin B12 in an amount of from about 0.10 weight percent to about 2.00 weight percent of the composition;

(i) vitamin C in an amount of from about 1.00 weight percent to about 5.00 weight percent of the composition;

(j) vitamin $D_3$ in an amount of from about 0.01 weight percent to about 0.50 weight percent of the composition;

(k) a pharmaceutically-acceptable compound of calcium in an amount of from about 10.00 weight percent to about 35.00 weight percent of the composition;

(l) a pharmaceutically-acceptable compound of magnesium in an amount of from about 25.00 weight percent to about 40.00 weight percent of the composition;

(m) a pharmaceutically-acceptable compound of zinc in an amount of from about 0.10 weight percent to about 1.00 weight percent of the composition;

(n) a pharmaceutically-acceptable compound of selenium in an amount of from about 0.01 weight percent to about 0.20 weight percent of the composition;

(o) a pharmaceutically-acceptable compound of iron in an amount of from about 0.10 weight percent to about 3.00 weight percent of the composition;

(p) a pharmaceutically-acceptable compound of L-carnitine in an amount of from about 20.00 weight percent to about 30.00 weight percent of the composition;

(q) a pharmaceutically-acceptable compound of manganese in an amount of from about 0.01 weight percent to about 0.20 weight percent of the composition;

(r) a pharmaceutically-acceptable compound of chromium in an amount of from about 0.001 weight percent to about 0.010 weight percent of the composition;

(s) a pharmaceutically-acceptable compound of copper in an amount of from about 0.01 weight percent to about 0.50 weight percent of the composition;

(t) glutathione or pharmaceutically-acceptable salt thereof in an amount of from about 1.00 weight percent to about 5.00 weight percent of the composition.

Aspect 3. The composition of Aspect 1, wherein the composition is unit dose composition comprising (a) vitamin B1 in an amount of from about 0.50 weight percent to about 3.00 weight percent of the composition;

(b) vitamin B2 in an amount of from about 0.50 weight percent to about 3.00 weight percent of the composition;

(c) vitamin B3 in an amount of from about 1.00 weight percent to about 3.00 weight percent of the composition;

(d) vitamin B5 in an amount of from about 0.10 weight percent to about 2.00 weight percent of the composition;

(e) vitamin B6 in an amount of from about 0.10 weight percent to about 2.00 weight percent of the composition;

(f) vitamin B7 in an amount of from about 0.10 weight percent to about 3.00 weight percent of the composition;

(g) vitamin B9 in an amount of from about 0.01 weight percent to about 0.10 weight percent of the composition;

(h) vitamin B12 in an amount of from about 1.00 weight percent to about 10.00 weight percent of the composition;

(i) vitamin C in an amount of from about 1.00 weight percent to about 10.00 weight percent of the composition;

(j) vitamin $D_3$ in an amount of from about 0.10 weight percent to about 1.00 weight percent of the composition;

(k) a pharmaceutically-acceptable compound of calcium in an amount of from about 15.00 weight percent to about 25.00 weight percent of the composition;

(l) a pharmaceutically-acceptable compound of magnesium in an amount of from about 5.00 weight percent to about 15.00 weight percent of the composition;

(m) a pharmaceutically-acceptable compound of zinc in an amount of from about 1.00 weight percent to about 5.00 weight percent of the composition;

(n) a pharmaceutically-acceptable compound of selenium in an amount of from about 0.10 weight percent to about 2.00 weight percent of the composition;

(o) a pharmaceutically-acceptable compound of iron in an amount of from about 5.00 weight percent to about 20.00 weight percent of the composition;

(p) a pharmaceutically-acceptable compound of L-carnitine in an amount of from about 10.00 weight percent to about 25.00 weight percent of the composition;

(q) a pharmaceutically-acceptable compound of manganese in an amount of from about 0.10 weight percent to about 1.00 weight percent of the composition;

(r) a pharmaceutically-acceptable compound of chromium in an amount of from about 0.001 weight percent to about 0.10 weight percent of the composition;

(s) a pharmaceutically-acceptable compound of copper in an amount of from about 0.10 weight percent to about 2.00 weight percent of the composition;

(t) glutathione or pharmaceutically-acceptable salt thereof in an amount of from about 5.00 weight percent to about 20.00 weight percent of the composition.

Aspect 4. The composition of Aspect 3, wherein the unit dose composition is from about 200 mg to about 800 mg, preferably about 500 mg.

Aspect 5. The composition of Aspect 3 or 4, wherein the unit oral dose composition is a capsule.

Aspect 6. The composition of any one of Aspects 1-5, wherein the pharmaceutically-acceptable compound of calcium is calcium citrate, calcium citrate tetrahydrate, calcium lactate pentahydrate, calcium ascorbate, calcium carbonate, or calcium oxide.

Aspect 7. The composition of any one of Aspects 1-6, wherein the pharmaceutically-acceptable compound of magnesium is magnesium citrate, magnesium sulfate monohydrate or heptahydrate, magnesium acetate tetrahydrate, magnesium D-gluconate hydrate, magnesium nitrate hexahydrate, or magnesium oxide.

Aspect 8. The composition of any one of Aspects 1-7, wherein the pharmaceutically-acceptable compound of zinc is zinc citrate, zinc citrate dihydrate, zinc acetate dihydrate, or zinc nitrate hexahydrate.

Aspect 9. The composition of any one of Aspects 1-8, wherein the pharmaceutically-acceptable compound of selenium is sodium selenate, sodium selenite, or L-selenomethionine.

Aspect 10. The composition of any one of Aspects 1-9, wherein the pharmaceutically-acceptable compound of iron is iron gluconate, iron gluconate dihydrate, or iron sulfate heptahydrate.

Aspect 11. The composition of any one of Aspects 1-10, wherein the pharmaceutically-acceptable compound of L-carnitine is L-carnitine-L-tartrate or acetyl-L-carnitine.

Aspect 12. The composition of any one of Aspects 1-11, wherein the pharmaceutically-acceptable compound of manganese is manganese citrate, manganese gluconate, manganese chloride.

Aspect 13. The composition of any one of Aspects 1-12, wherein the pharmaceutically-acceptable compound of chromium is chromium picolinate.

Aspect 14. The composition of any one of Aspects 1-13, wherein the pharmaceutically-acceptable compound of copper is copper gluconate.

Aspect 15. The composition of any one of Aspects 1-14, wherein the pharmaceutically-acceptable compound of calcium is calcium citrate, the pharmaceutically-acceptable compound of magnesium is magnesium citrate, the pharmaceutically-acceptable compound of zinc is zinc citrate; the pharmaceutically-acceptable compound of selenium is sodium selenate; the pharmaceutically-acceptable compound of iron is iron gluconate; the pharmaceutically-acceptable compound of manganese is manganese citrate; the pharmaceutically-acceptable compound of chromium is chromium picolinate; and the pharmaceutically-acceptable compound of copper is copper gluconate.

Aspect 16. The composition of any one of Aspects 1-15, wherein the composition further comprises alpha lipolic acid, red beetroot extract, sugar beet pectin, a pharmaceutically-acceptable compound of boron, and apple pectin.

Aspect 17. The composition of Aspect 16, wherein alpha lipolic acid is present in the composition in an amount of from about 1.00 weight percent to about 10.00 weight percent of the composition.

Aspect 18. The composition of Aspect 16, wherein red beetroot extract is present in the composition in an amount of from about 1.00 weight percent to about 15.00 weight percent of the composition.

Aspect 19. The composition of Aspect 16, wherein the pharmaceutically-acceptable compound of boron is present in the composition in an amount of from about 0.001 weight percent to about 0.05 weight percent of the composition.

Aspect 20. The composition of Aspect 16, wherein the pharmaceutically-acceptable compound of boron is boroglycinate or sodium tetraborate.

Aspect 21. The composition of Aspect 16, wherein the apple pectin is present in the composition in an amount of from about 1.00 weight percent to about 10.00 weight percent of the composition.

Aspect 22. The composition of claim 16, wherein the sugar beet pectin is present in the composition in an amount of from about 0.5 weight percent to about 5.00 weight percent of the composition.

Aspect 23. A composition comprising
   (a) vitamin B1
   (b) vitamin B2
   (c) vitamin B3
   (d) vitamin B5
   (e) vitamin B6
   (f) vitamin B7
   (g) vitamin B9
   (h) vitamin B12
   (i) vitamin C
   (j) vitamin $D_3$
   (k) a pharmaceutically-acceptable compound of calcium
   (l) a pharmaceutically-acceptable compound of magnesium
   (m) a pharmaceutically-acceptable compound of zinc
   (n) a pharmaceutically-acceptable compound of selenium
   (o) a pharmaceutically-acceptable compound of iron
   (p) a pharmaceutically-acceptable compound of L-carnitine
   (q) apple pectin.

Aspect 24. The composition of Aspect 23, wherein the composition comprises
   (a) vitamin B1 in an amount of from about 0.005 weight percent to about 0.10 weight percent of the composition;
   (b) vitamin B2 in an amount of from about 0.005 weight percent to about 0.10 weight percent of the composition;
   (c) vitamin B3 in an amount of from about 0.05 weight percent to about 0.50 weight percent of the composition;
   (d) vitamin B5 in an amount of from about 0.01 weight percent to about 0.50 weight percent of the composition;
   (e) vitamin B6 in an amount of from about 0.01 weight percent to about 0.50 weight percent of the composition;
   (f) vitamin B7 in an amount of from about 0.010 weight percent to about 0.50 weight percent of the composition;
   (g) vitamin B9 in an amount of from about 0.001 weight percent to about 0.10 weight percent of the composition;
   (h) vitamin B12 in an amount of from about 0.05 weight percent to about 0.50 weight percent of the composition;

(i) vitamin C in an amount of from about 1.00 weight percent to about 10.00 weight percent of the composition;

(j) vitamin D₃ in an amount of from about 0.01 weight percent to about 0.50 weight percent of the composition;

(k) a pharmaceutically-acceptable compound of calcium in an amount of from about 10.00 weight percent to about 35.00 weight percent of the composition;

(l) a pharmaceutically-acceptable compound of magnesium in an amount of from about 15.00 weight percent to about 35.00 weight percent of the composition;

(m) a pharmaceutically-acceptable compound of zinc in an amount of from about 0.10 weight percent to about 2.00 weight percent of the composition;

(n) a pharmaceutically-acceptable compound of selenium in an amount of from about 0.01 weight percent to about 0.50 weight percent of the composition;

(o) a pharmaceutically-acceptable compound of iron in an amount of from about 0.05 weight percent to about 5.00 weight percent of the composition;

(p) a pharmaceutically-acceptable compound of L-carnitine in an amount of from about 10.00 weight percent to about 30.00 weight percent of the composition;

(q) apple pectin in an amount of from about 1.00 weight percent to about 10.00 weight percent of the composition.

Aspect 25. The composition of Aspect 23 or 24, wherein the composition includes a pharmaceutically-acceptable compound of chromium.

Aspect 26. The composition of Aspect 25, wherein the pharmaceutically-acceptable compound of chromium in an amount of from about 0.0001 weight percent to about 0.001 weight percent of the composition;

Aspect 27. A composition comprising (a) vitamin B1
(b) vitamin B2
(c) vitamin B3
(d) vitamin B5
(e) vitamin B6
(f) vitamin B7
(g) vitamin B9
(h) vitamin B12
(i) vitamin C
(j) vitamin D₃
(k) a pharmaceutically-acceptable compound of calcium
(l) a pharmaceutically-acceptable compound of magnesium
(m) a pharmaceutically-acceptable compound of zinc
(n) a pharmaceutically-acceptable compound of selenium
(o) a pharmaceutically-acceptable compound of iron
(p) a pharmaceutically-acceptable compound of L-carnitine
(q) a pharmaceutically-acceptable compound of L-arginine
(r) a pharmaceutically-acceptable compound of L-citruline(s)
(s) red beetroot extract
(t) a pharmaceutically-acceptable compound of boron
(u) glutathione or pharmaceutically-acceptable salt thereof
(v) apple pectin.

Aspect 28. The composition of Aspect 27, wherein the composition comprises (a) vitamin B1 in an amount of from about 0.10 weight percent to about 0.50 weight percent of the composition;

(b) vitamin B2 in an amount of from about 0.10 weight percent to about 0.50 weight percent of the composition;

(c) vitamin B3 in an amount of from about 0.10 weight percent to about 0.50 weight percent of the composition;

(d) vitamin B5 in an amount of from about 0.01 weight percent to about 0.50 weight percent of the composition;

(e) vitamin B6 in an amount of from about 0.01 weight percent to about 0.50 weight percent of the composition;

(f) vitamin B7 in an amount of from about 0.10 weight percent to about 1.00 weight percent of the composition;

(g) vitamin B9 in an amount of from about 0.001 weight percent to about 0.10 weight percent of the composition;

(h) vitamin B12 in an amount of from about 0.10 weight percent to about 2.00 weight percent of the composition;

(i) vitamin C in an amount of from about 1.00 weight percent to about 5.00 weight percent of the composition;

(j) vitamin D₃ in an amount of from about 0.01 weight percent to about 0.50 weight percent of the composition;

(k) a pharmaceutically-acceptable compound of calcium in an amount of from about 10.00 weight percent to about 35.00 weight percent of the composition;

(l) a pharmaceutically-acceptable compound of magnesium in an amount of from about 25.00 weight percent to about 40.00 weight percent of the composition;

(m) a pharmaceutically-acceptable compound of zinc in an amount of from about 0.10 weight percent to about 1.00 weight percent of the composition;

(n) a pharmaceutically-acceptable compound of selenium in an amount of from about 0.01 weight percent to about 0.20 weight percent of the composition;

(o) a pharmaceutically-acceptable compound of iron in an amount of from about 0.10 weight percent to about 3.00 weight percent of the composition;

(p) a pharmaceutically-acceptable compound of L-carnitine in an amount of from about 20.00 weight percent to about 30.00 weight percent of the composition;

(q) glutathione or pharmaceutically-acceptable salt thereof in an amount of from about 1.00 weight percent to about 5.00 weight percent of the composition (r) a pharmaceutically-acceptable compound of L-arginine in an amount of from about 1.00 weight percent to about 10.00 weight percent of the composition;

(s) a pharmaceutically-acceptable compound of L-citruline in an amount of from about 1.00 weight percent to about 10.00 weight percent of the composition;

(t) a pharmaceutically-acceptable compound of boron in an amount of from about 0.001 weight percent to about 0.050 weight percent of the composition;

(u) red beetroot extract in an amount of from about 1.00 weight percent to about 15.00 weight percent of the composition;

(v) apple pectin in an amount of from about 1.00 weight percent to about 10.00 weight percent of the composition.

Aspect 29. The composition of Aspect 27, wherein the composition is unit dose composition comprising (a) vitamin B1 in an amount of from about 0.50 weight percent to about 3.00 weight percent of the composition;

(b) vitamin B2 in an amount of from about 0.50 weight percent to about 3.00 weight percent of the composition;

(c) vitamin B3 in an amount of from about 1.00 weight percent to about 3.00 weight percent of the composition;

(d) vitamin B5 in an amount of from about 0.10 weight percent to about 2.00 weight percent of the composition;

(e) vitamin B6 in an amount of from about 0.10 weight percent to about 2.00 weight percent of the composition;

(f) vitamin B7 in an amount of from about 0.10 weight percent to about 3.00 weight percent of the composition;

(g) vitamin B9 in an amount of from about 0.01 weight percent to about 0.10 weight percent of the composition;

(h) vitamin B12 in an amount of from about 1.00 weight percent to about 10.00 weight percent of the composition;

(i) vitamin C in an amount of from about 1.00 weight percent to about 10.00 weight percent of the composition;

(j) vitamin $D_3$ in an amount of from about 0.10 weight percent to about 1.00 weight percent of the composition;

(k) a pharmaceutically-acceptable compound of calcium in an amount of from about 15.00 weight percent to about 25.00 weight percent of the composition;

(l) a pharmaceutically-acceptable compound of magnesium in an amount of from about 5.00 weight percent to about 15.00 weight percent of the composition;

(m) a pharmaceutically-acceptable compound of zinc in an amount of from about 1.00 weight percent to about 5.00 weight percent of the composition;

(n) a pharmaceutically-acceptable compound of selenium in an amount of from about 0.10 weight percent to about 2.00 weight percent of the composition;

(o) a pharmaceutically-acceptable compound of iron in an amount of from about 5.00 weight percent to about 20.00 weight percent of the composition;

(p) a pharmaceutically-acceptable compound of L-carnitine in an amount of from about 10.00 weight percent to about 25.00 weight percent of the composition;

(q) glutathione or pharmaceutically-acceptable salt thereof in an amount of from about 5.00 weight percent to about 20.00 weight percent of the composition.

(r) a pharmaceutically-acceptable compound of L-arginine in an amount of from about 4.00 weight percent to about 5.00 weight percent of the composition;

(s) a pharmaceutically-acceptable compound of L-citrulline in an amount of from about 4.00 weight percent to about 5.00 weight percent of the composition;

(t) a pharmaceutically-acceptable compound of boron in an amount of from about 0.005 weight percent to about 0.02 weight percent of the composition;

(u) red beetroot extract in an amount of from about 7.00 weight percent to about 8.00 weight percent of the composition;

(v) apple pectin in an amount of from about 7.00 weight percent to about 8.00 weight percent of the composition;

Aspect 30. A composition comprising (a) vitamin B1

(b) vitamin B2

(c) vitamin B3

(d) vitamin B5

(e) vitamin B6

(f) vitamin B7

(g) vitamin B9

(h) vitamin B12

(i) vitamin C (j) vitamin $D_3$ (k) a pharmaceutically-acceptable compound of calcium (l) a pharmaceutically-acceptable compound of magnesium (m) a pharmaceutically-acceptable compound of zinc (n) a pharmaceutically-acceptable compound of selenium (o) a pharmaceutically-acceptable compound of iron (p) a pharmaceutically-acceptable compound of L-carnitine (q) a pharmaceutically-acceptable compound of L-arginine (r) a pharmaceutically-acceptable compound of L-citrulline(s)

(s) red beetroot extract (t) a pharmaceutically-acceptable compound of boron (u) glutathione or pharmaceutically-acceptable salt thereof (v) sugar beet pectin pectin (w) alpha lipoic acid.

Aspect 31. The composition of Aspect 30, wherein the composition comprises (a) vitamin B1 in an amount of from about 0.010 weight percent to about 0.050 weight percent of the composition;

(b) vitamin B2 in an amount of from about 0.010 weight percent to about 0.050 weight percent of the composition;

(c) vitamin B3 in an amount of from about 0.10 weight percent to about 0.50 weight percent of the composition;

(d) vitamin B5 in an amount of from about 0.01 weight percent to about 0.50 weight percent of the composition;

(e) vitamin B6 in an amount of from about 0.01 weight percent to about 0.50 weight percent of the composition;

(f) vitamin B7 in an amount of from about 0.05 weight percent to about 1.00 weight percent of the composition;

(g) vitamin B9 in an amount of from about 0.001 weight percent to about 0.10 weight percent of the composition;

(h) vitamin B12 in an amount of from about 0.05 weight percent to about 2.00 weight percent of the composition;

(i) vitamin C in an amount of from about 1.00 weight percent to about 5.00 weight percent of the composition;

(j) vitamin $D_3$ in an amount of from about 0.01 weight percent to about 0.50 weight percent of the composition;

(k) a pharmaceutically-acceptable compound of calcium in an amount of from about 10.00 weight percent to about 35.00 weight percent of the composition;

(l) a pharmaceutically-acceptable compound of magnesium in an amount of from about 15.00 weight percent to about 40.00 weight percent of the composition;

(m) a pharmaceutically-acceptable compound of zinc in an amount of from about 0.10 weight percent to about 2.00 weight percent of the composition;

(n) a pharmaceutically-acceptable compound of selenium in an amount of from about 0.10 weight percent to about 1.50 weight percent of the composition;

(o) a pharmaceutically-acceptable compound of iron in an amount of from about 0.50 weight percent to about 5.00 weight percent of the composition;

(p) a pharmaceutically-acceptable compound of L-carnitine in an amount of from about 10.00 weight percent to about 30.00 weight percent of the composition;

(q) glutathione or pharmaceutically-acceptable salt thereof in an amount of from about 0.50 weight percent to about 5.00 weight percent of the composition (r) a pharmaceutically-acceptable compound of L-arginine in an amount of from about 1.00 weight percent to about 10.00 weight percent of the composition;

(s) a pharmaceutically-acceptable compound of L-citrulline in an amount of from about 1.00 weight percent to about 10.00 weight percent of the composition;

(t) a pharmaceutically-acceptable compound of boron in an amount of from about 0.001 weight percent to about 0.20 weight percent of the composition;

(u) red beetroot extract in an amount of from about 1.00 weight percent to about 15.00 weight percent of the composition;

(v) sugar beet pectin in an amount of from about 0.50 weight percent to about 5.00 weight percent of the composition; and (w) alpha lipoic acid in an amount of from about 1.00 weight percent to about 10.00 weight percent of the composition.

Aspect 32. The composition of Aspect 30, wherein the composition is unit dose composition comprising (a) vitamin B1 in an amount of from about 0.10 weight percent to about 0.03 weight percent of the composition;

(b) vitamin B2 in an amount of from about 0.10 weight percent to about 0.30 weight percent of the composition;

(c) vitamin B3 in an amount of from about 0.20 weight percent to about 0.30 weight percent of the composition;

(d) vitamin B5 in an amount of from about 0.0.05 weight percent to about 0.30 weight percent of the composition;

(e) vitamin B6 in an amount of from about 0.01 weight percent to about 1.50 weight percent of the composition;

(f) vitamin B7 in an amount of from about 0.05 weight percent to about 0.30 weight percent of the composition;

(g) vitamin B9 in an amount of from about 0.001 weight percent to about 0.02 weight percent of the composition;

(h) vitamin B12 in an amount of from about 0.05 weight percent to about 0.50 weight percent of the composition;

(i) vitamin C in an amount of from about 1.00 weight percent to about 5.00 weight percent of the composition;

(j) vitamin D₃ in an amount of from about 0.10 weight percent to about 1.00 weight percent of the composition;

(k) a pharmaceutically-acceptable compound of calcium in an amount of from about 15.00 weight percent to about 25.00 weight percent of the composition;

(l) a pharmaceutically-acceptable compound of magnesium in an amount of from about 15.00 weight percent to about 25.00 weight percent of the composition;

(m) a pharmaceutically-acceptable compound of zinc in an amount of from about 0.50 weight percent to about 1.50 weight percent of the composition;

(n) a pharmaceutically-acceptable compound of selenium in an amount of from about 0.10 weight percent to about 2.00 weight percent of the composition;

(o) a pharmaceutically-acceptable compound of iron in an amount of from about 1.00 weight percent to about 5.00 weight percent of the composition;

(p) a pharmaceutically-acceptable compound of L-carnitine in an amount of from about 15.00 weight percent to about 25.00 weight percent of the composition;

(q) glutathione or pharmaceutically-acceptable salt thereof in an amount of from about 1.00 weight percent to about 4.00 weight percent of the composition.

(r) a pharmaceutically-acceptable compound of L-arginine in an amount of from about 3.00 weight percent to about 8.00 weight percent of the composition;

(s) a pharmaceutically-acceptable compound of L-citrulline in an amount of from about 3.00 weight percent to about 8.00 weight percent of the composition;

(t) a pharmaceutically-acceptable compound of boron in an amount of from about 0.010 weight percent to about 0.015 weight percent of the composition;

(u) red beetroot extract in an amount of from about 5.00 weight percent to about 7.00 weight percent of the composition;

(v) sugar beet pectin in an amount of from about 2.00 weight percent to about 3.00 weight percent of the composition; and alpha lipoic acid in an amount of from about 3.00 weight percent to about 4.00 weight percent of the composition.

Aspect 33. The composition of any one of Aspects 27 to 32, wherein the composition further comprises a pharmaceutically-acceptable compound of chromium.

Aspect 34. The composition of Aspect 33, wherein the pharmaceutically-acceptable compound of chromium in an amount of from about 0.001 weight percent to about 0.010 weight percent of the composition.

Aspect 35. The composition of any one of Aspects 1-34, wherein the composition further comprises a citrus bioflavonoid, a powdered extract of cranberry and/or cherry, or a combination thereof.

Aspect 36. The composition of any one of Aspects 1-35, wherein the composition comprises a dry powder.

Aspect 37. The composition of any one of Aspects 1-36, wherein the composition further comprises a polysaccharide filler.

Aspect 38. The composition of Aspect 37, wherein the polysaccharide filler comprises maltodextrin.

Aspect 39. The composition of any one of Aspects 1-38, wherein the composition does not include a pharmaceutically-acceptable compound of potassium, sodium, or phosphorous.

Aspect 40. A kit comprising (a) the composition of any one of Aspects 1-39; and (b) a marine omega 3 fatty acid, coenzyme Q10, or a combination thereof.

Aspect 41. The kit of Aspect 40, wherein the marine omega 3 fatty acids comprise DHA and EPA in the weight ratio (EPA:DHA) of 1:1 to 4:1.

Aspect 42. The kit of Aspect 40 or 41, wherein the marine omega 3 fatty acids are in the amount of 500 mg to 4,000 mg per unit dose.

Aspect 43. The kit of any one of Aspects 40-42, wherein coenzyme Q10 is ubiquinol.

Aspect 44. The kit of any one of Aspects 40-42, wherein the coenzyme Q10 is in the amount of 70 mg to 400 mg per unit dose.

Aspect 45. The kit of any one of Aspects 40-44, wherein the kit optionally comprises a capsule comprising turmeric, wherein the turmeric is in the amount of 1 g to 3 g per unit dose.

Aspect 46. A method for treating a subject with type I diabetes or type II diabetes or a subject diagnosed with prediabetes, the method comprising administering to the subject the composition in any of Aspects 1-39.

Aspect 47. The method of Aspect 46, wherein the composition reduces or prevents one or more symptoms of type I diabetes or type II diabetes when compared to the same subject prior to the administration of the composition.

Aspect 48. The method of Aspect 47, wherein the symptom is weight loss, polydipsia, polyuria, polyphagia, blurred vision, headache, fatigue, slow healing of cuts, itchy skin, or any combination thereof.

Aspect 49. The method of Aspect 46, wherein the composition reduces the amount of insulin required by the subject.

Aspect 50. A method for improving the health of a subject undergoing dialysis comprising administering to the subject the composition in any of Aspects 1-39.

Aspect 51. The method of Aspect 50, wherein the composition provides one or more benefits after dialysis when compared to the same subject prior to the administration of the composition: improved recovery after dialysis treatment, increased body strength, improved appetite, improved sleep, reduced pain in the body preferably in joints.

Aspect 52. A method for treating myalgic encephalomyelitis in a subject of comprising administering to the subject the composition in any of Aspects 1-39.

Aspect 53. The method of Aspect 52, wherein the composition reduces or prevents one or more symptoms of myalgic encephalomyelitis, wherein the symptom comprises extreme tiredness, difficulty with sleeping, feeling dizzy or sick, sore throat, flu-like symptoms, heart palpitations, muscle or joint pain, headaches, difficulty with thinking, memory and concentration, mental fog and fatigue, and any combination thereof.

Aspect 54. A method for enhancing one or more physical properties of a subject after exercise comprising administering to the subject the composition in any of Aspects 1-39 before and/or after exercise.

Aspect 55. The method of Aspect 54, wherein the physical property comprises improved recovery after exercise, increased energy, increased body strength, improved appetite, improved sleep, reduced muscle and joint pain, or any combination thereof.

Aspect 56. A method for reducing or preventing one or more symptoms of Crohn's disease in a subject of comprising administering to the subject the composition in any of Aspects 1-39.

Aspect 57. The method of any one of Aspects 46-56, wherein the subject is administered from about 1 gram to about 2 grams of the composition daily.

Aspect 58. The method of any one of Aspects 46-57, further comprising administering to the subject marine omega 3 fatty acids, coenzyme Q10, or a combination thereof.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure.

I. Sport Supplement Evaluation (Renusport)

A sport supplement as described herein (referred to as RenuSport") and provided in Table 1 was evaluated. "RenuSport" is a recently developed supplement that is aimed at elite athletes or very active athletes who perform regular, intensive or heavy training. "RenuSport" is a uniquely formulated supplement with a focus on improved recovery after training, increased energy levels, increased endurance and strength and reduced muscle and joint pain. In addition to a large number of important vitamins and minerals, "RenuSport" contains some very specific components that contribute positively to improving recovery after exercise, especially training pain, endurance and lactic acid dissipation.

TABLE 1

| Ingredient | Amount (%) | Component | Amount per unit dose |
|---|---|---|---|
| Magnesium Citrate | 21.0953 | Magnesium | 260 mg |
| Tricalcium Citrate | 18.1448 | Calcium | 325 mg |
| L-Carnitine L-Tartrate | 21.3103 | L-Carnitine | 1214 mg |
| Maltodextrin | 4.5726 | Polysaccharide | 5 mg |
| Ascorbic Acid | 2.811 | Vitamin C | 200 mg |
| Ferrous Gluconate | 2.4382 | Iron | 24 mg |
| Citrus Bioflavonoid Complex | 0.5882 | Citrus | 50 mg |
| Zinc Citrate | 0.9152 | Zinc | 25 mg |
| Niacinamide | 0.2614 | Vitamin B3 | 20 mg |
| Calcium D-Pantothenate | 0.1487 | Vitamin B5 | 10 mg |
| D-Biotin 1% Trituration on Maltodextrin | 0.1412 | Vitamin B7 | 0.1 mg |
| Cyanocobalamin, 01.% | 0.2205 | Vitamin B12 | 15 mcg |
| 0.5% L. Selenomethionine | 0.7880 | Selenium | 140 mcg |
| Pyridoxine HCl | 0.0787 | Vitamin B6 | 5 mg |
| Lanolin | 0.5409 | Vitamin D3 | 100 mcg |
| Thiamine Mononitrate | 0.0255 | Vitamin B1 | 1.5 mg |
| Riboflavin | 0.0242 | Vitamin B2 | 1.7 mg |
| Folic Acid | 0.0097 | Vitamin B9 | 0.6 mg |
| Reduced Glutathione | 2.0000 | Glutathione | 170 mg |
| L-Arginine | 5.8820 | L-Arginine | 500 mg |
| L-Citrulline | 5.8820 | L-Citrulline | 500 mg |
| Sodium Tetraborate | 0.0822 | Boron | 1.5 mg |
| Sugarbeet Pectin | 2.4000 | Pectin | 200 mg |
| Alpha Lipoic Acid | 3.5300 | Lipoic Acid | 300 mg |
| Red Beet Extract | 6.0373 | Red Beet Extract | 520 mg |

To systematically document the effects that can be achieved by using the "RenuSport" supplement, an evaluation among 25 participants has been carried out.

The evaluation is based on well-proven methods that are used in quality-of-life surveys as well as previous experience with evaluations.

The participants were initially contacted for their health and background status in a survey interview. An agreement was signed and each participant received three months' supply of the "RenuSport" supplement. After 1, 2 and 3 months, the participants answered a questionnaire with questions about their training and the feeling of recovery, endurance, post-workout soreness, lactic acid cramps and whether anything else had changed.

The evaluation had 25 participants, consisting of 9 women and 16 men. An initial objective was to have an even distribution between gender and age, including a variety of sports activities. In terms of age, there is a spread between the youngest participant, 19 years old, to the oldest, 61 years old. Further, all of the participants who took part in the evaluation are active in sports such as handball at elite level (5 women), floorball at elite level (7 men, 1 woman) and a mixed group (3 women and 9 men) who play soccer and do exercises in the gym, e.g. CrossFit, cycling/spinning, running etc. Three participants did not complete the evaluation.

1. 49-year-old male who has always exercised, an "all-around athlete" and former racquet sports player. He suffered a knee injury and switched to road cycling and spinning and exercises four times a week. His evaluation after one month showed less discomfort during exercise, better endurance, and faster recovery. In the second evaluation, the participant was ill for almost the entire month and, therefore, was not able to exercise. By the third evaluation, the participant was back in training and could again feel that endurance and recovery had improved.

2. 24-year-old female who plays floorball at an elite level and trains about 4-5 sessions a week and has a match 1-2 times a week. After taking "RenuSport" for a month, her recovery after exercise has improved. Further, she did not feel as tired the day after a game or hard training and the lactic acid did not bother her much. After two months, she continued to feel more energetic and was less tired in the body. Additionally, the training pains have decreased and she felt that she slept much better. In the third evaluation, she had a knee injury and is currently involved in a rehab program. However, she continues to feel alert, and her sleep has improved.

3. 31-year-old male who is physically active and combines study and work. He has tried many different sports but now focuses on CrossFit and trains 4-5 days a week. In the initial evaluation, he was busy at work and school and exercised twice a week; however, he felt that he recovered from muscle spasms much faster. In the second evaluation, his workload was reduced, thus his training increased, and his recovery was still fast. In the third evaluation, the participant felt that he was not as tired at work. Moreover, he reported that he felt he wasn't tired at work and his post-exercise soreness didn't bother him as much, plus he wasn't getting muscle soreness as before taking the supplement.

4. 19-year-old male who is physically active and has a job that is physically demanding. He works out 5-6 times a week at the gym, running and soccer at a high level. In the first evaluation, he felt more energetic and had less exercise pain. He also felt that endurance and recovery had been somewhat improved in the second evaluation. In the third evaluation, he reported that his sleep pattern has improved, and that endurance and recovery remained as good as in the second evaluation.

5. 48-year-old male who is a former professional ice hockey player. He is now very active, approximately 10-14 practice sessions per week with power walk, gym, golf and padel. After taking the supplement for three months, he felt no major changes in endurance and recovery except that he slept much better, deeper, and without interruptions.

6. 33-year-old female who works as a group training instructor and works out about 6 training sessions a week. When evaluated after one month, she felt that her recovery had improved and that exercise soreness and lactic acid had decreased. Her evaluation was the same after two months; however, in the third evaluation, she had stepped up her training to 7 times a week and she experienced a significant difference in her recovery. She reported that previously, she was limited by training pains, which have now decreased, and her endurance has improved.

7. 51-year-old male who is active and works out 10 times a week. His training regimen includes strength training, running, disc golf, and he does at least 20,000 steps on the pedometer every day. In the first two evaluations, he reported no difference. In the third evaluation, there was a small difference in recovery and exercise soreness; however, he felt less lactic acid and less cramps at night.

8. 30-year-old female who previously played soccer but stopped due to injury. Today, she trains 4-6 times per week, including three spinning sessions. After one month, her endurance and recovery were greatly improved, and she felt that the training pains were reduced. The second evaluation showed the same good results; however, in the third evaluation, she described her recovery as much better than before and she didn't feel the training pains in the same way as before. Further, she felt stronger and had longer endurance and slept much better. She was very grateful and satisfied with the results.

9. 28-year-old male who has always worked out and is currently working and playing floorball in the top league. He trains 5-6 times a week plus games. In the first evaluation, he felt less tired, a notable difference, and his endurance has also improved. After two months, his endurance and recovery were still better; however, after three months, he felt that he could go all out on several training sessions a week without feeling completely exhausted.

10. 20-year-old male who is a former soccer player, but now a floorball player in the highest league and has always worked out since a young age. He trains 4-6 times a week, plus games. After one month, he stated that his endurance has improved and that he did not get lactic acid cramps as easily as before. However, he had been ill for a week in the second evaluation but felt the same improvement in endurance with less lactic acid. In the third evaluation, the participant reported that his recovery has greatly improved since he started "RenuSport".

11. 20-year-old male who played soccer for several years and for the last four years has played floorball at an elite level and trains about seven times a week. After one month, he felt that his endurance had slightly improved and that he was not getting as much lactic acid. After two months, the training pains were notably reduced and he reported that he slept better and felt refreshed when he woke up. In the third evaluation, the participant had a cold but still felt that endurance, lactic acid, and exercise soreness were affected in a positive way.

12. 19-year-old male who is a floorball player at an elite level and trains 5-6 times a week, plus games. In the first evaluation, the participant felt that he slept better and felt more rejuvenated when he woke up. After two months, his recovery was the same as before; however, he reported that his training pains dissipated faster, and his endurance had improved. After three months, he felt livelier and more energetic.

13. 39-year-old male who has a demanding job, has practiced floorball for 25 years and is active at an elite level. In the past two years, he has also been focusing on mobility exercises at the gym and he trains about 4-5 times a week. After taking "RenuSport" for one month and having a heavy workload, he felt more alert and reported that the muscles and joint pain he experienced during strenuous tasks has decreased. The participant also stated that he had an easier time falling asleep and felt rejuvenated when he woke up. After two months, he noticed a consistent improvement in his recovery and no longer experienced shortness of breath. He reported the same good results in the third evaluation.

14. 30-year-old male who is studying and practicing floorball at an elite level, has been training since he was very young, and currently trains about 10 times a week. After one month, he reported feeling significantly less pain after training. In his second evaluation, he noticed a slight improvement in his endurance. However, in his third evaluation, his results were still good, improved endurance and less pain after exercising.

15. 47-year-old male who is a former ice-hockey player at an elite level. Today, he engages in physical activities like powerwalking and running, and trains about seven times a week. After one month, he felt more energetic and he noted that there was a slight improvement in his endurance and post-exercise recovery. In the second evaluation, the improvements in his endurance and recovery remained the same. After three months, he reported that his endurance and post-exercise recovery had remarkably improved. The participant noted that his overall well-being was substantially greater than before and he felt better trained.

16. 21-year-old female who started dancing at the age of three, has played handball for the past 10 years and is currently in the highest division. She trains about six times a week, plus games. The participant was injured and she underwent rehab training during the first two months. In the last evaluation, she described regaining the energy and strength she had prior to her injury. She reported having a faster recovery and noted that her body's endurance was much better than before.

17. 23-year-old female who has practiced handball since she was very young and currently plays in the highest league while also going to college. She trains six times a week plus matches. In the first evaluation, she reported feeling more rejuvenated the day after her matches, and she experienced an improvement in her endurance. In the second evaluation, her progress remained the same, but she described feeling slightly less pain post-training. After three months, the participant's recovery and endurance were still better than before she took "RenuSport". She noted that there was a change in her sleeping patterns and felt that she was getting better and deeper sleep.

18. 25-year-old female who is an elite handball player, has been playing handball since she was twelve and trains about six times a week, plus games. After one month, she felt livelier and had more energy during the day. In the second evaluation, the participant underwent heavier training, and she did not notice a significant difference in her endurance or recovery. In her third evaluation, she was injured and did not train as usual. However, she felt good about taking the supplement.

19. 25-year-old female who is an elite handball player, a student, and has played handball since she was a child. She trains six times a week, plus games. After one month, she felt that she recovered much faster after strenuous sessions, and she also noted that her training pains did not last as they did before. She reported an improvement in her energy level and felt livelier during the day and evening. After two months, she continued to feel more energetic. Further, recovery was quicker and the pain she typically felt after training was reduced. In the last evaluation, soreness after exercise, lactic acid dissipation, and endurance had improved.

20. 20-year-old female who is an elite handball player has been playing handball since a young age and trains about six times a week, plus games. After one month, the participant felt that she recovered better and had less pain after training. After two months, including a two-week Christmas break where she engaged in her own personal training, she reported that her results remained the same. In the third evaluation, when she went back to full training sessions, she likened her recovery to what she experienced then after the first month of "RenuSport". Moreover, she has little to no training pains at all now, despite engaging in more physically demanding activities than she did previously.

21. 56-year-old male who has played soccer at an elite level and now trains about 5-8 times a week. His daily regimen includes strength training and conditioning. The participant did not experience any changes after taking "RenuSport" for three months.

22. 40-year-old male who has always been active, is a former elite level athlete and trains about 3-4 times a week. In the first evaluation, the participant was ill and consequently, didn't train. However, he felt better after two months and began exercising again but did not notice any changes. In the third evaluation, the participant revealed that he did not take the supplement properly and that this may have contributed to the lack of improvement in his endurance and post-exercise recovery.

Results and Discussion

Figure 2:
FIG. 2 shows the four areas evaluated versus participants' positive responses (percentage) when taking RenuSport.

Referring to FIG. 1, 79% of the males and 100% of the females experienced a tangible change in two or more areas evaluated. FIG. 2 shows the four areas that were evaluated. FIG. 2 clearly shows the great and tangible benefits that the participants who completed the evaluation had experienced. Additionally, most of the participants stated their overall well-being was substantially greater than before, and most felt better trained.

Figure 3:
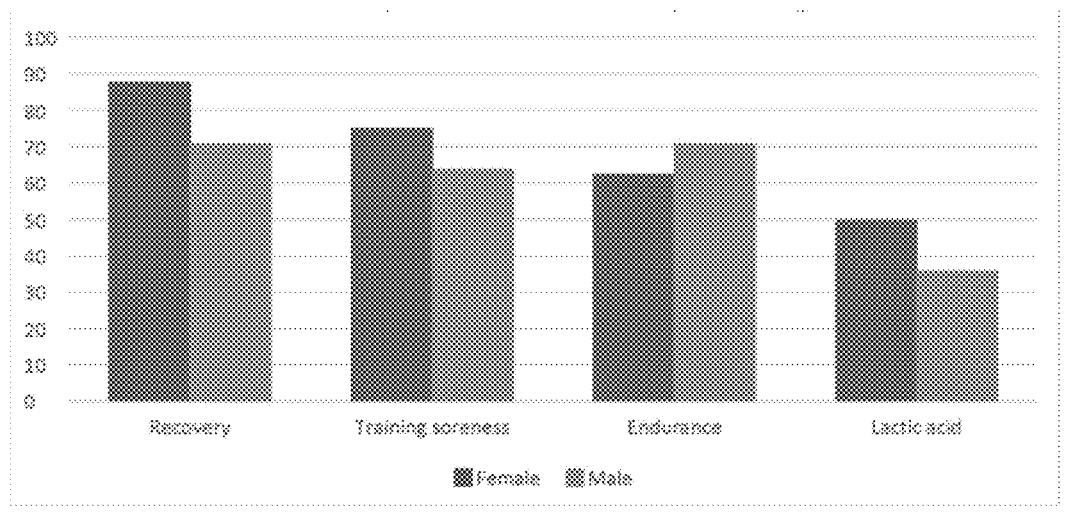
FIG. 3 shows the difference in gender response participants' positive responses (percentage) when taking RenuSport.

FIG. 3 shows the response differences between gender. Females were generally more positive in their answers than the males. One of the reasons the females had more positive experiences than the males may be due to the fact that the females were, in general, younger in addition to having more elite athletes among them.

Figure 4:
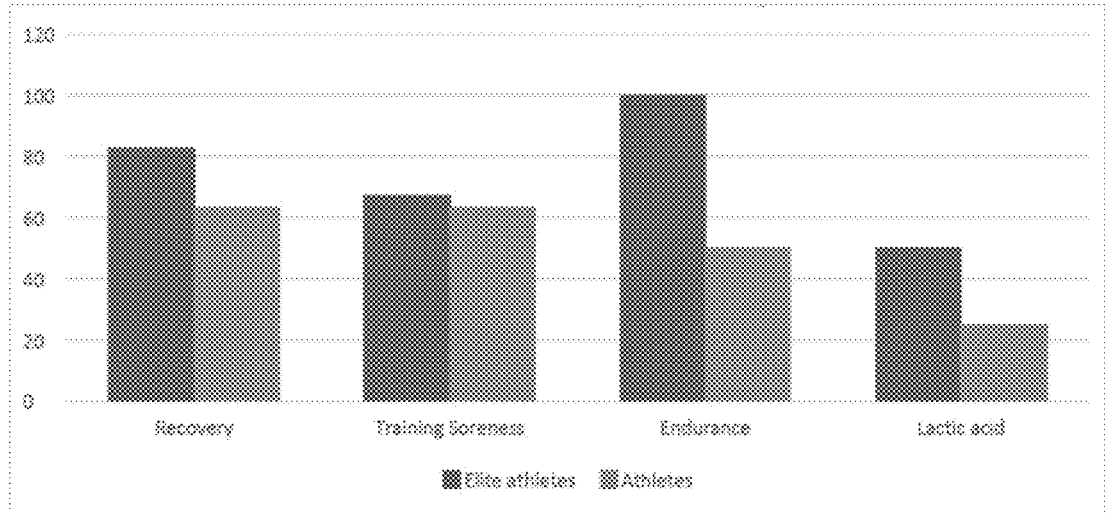
FIG. 4 shows the difference between elite athlete and athlete response when taking RenuSport.

FIG. 4 compares the groups that benefited the most from the supplement, i.e. the elite athletes versus athletes, among the female and male participants. The elite athletes evidently outperformed the athletes in all four categories, most prominently endurance, recovery, and lactic acid.

A closer look at the testimony of the 22 participants showed that nineteen participants experienced good to excellent results, this represented 86% success. This evaluation clearly demonstrates that "RenuSport" contributed positively, in several ways, to the health and well-being of those who participated in the evaluation; moreover, this resulted in the following benefits:

Improved and faster recovery after training.

Increased endurance and strength after strenuous sessions.

Less post-workout muscle soreness and joint pain.

Easier and faster lactic acid cramps dissipation.

More alert and slept better and deeper.

Felt livelier and more energetic.

Better overall well-being as well as better training.

II. Prediabetic/Diabetic Supplement Evaluation (Innucare)

A supplement as described herein (referred to as Innu-Care") and provided in Table 2 was evaluated. "InnuCare" is a recently developed supplement that is aimed to help both prediabetics as well as type I and type II diabetes patients. Pre-diabetics need a supplement that helps stabilize the sugar levels in the blood, thus helping the pre-diabetics to avoid slipping further. However, diabetics I and II need a supplement that improves their overall health as well as prevent them from slipping into insulin uptake. Thus, a combined supplement that would address both issues as well as other related issues to diabetes and insulin uptake was our objective for developing InuCare.

TABLE 2

| Ingredient | Amount (%) | Component | Amount per unit dose | |
| --- | --- | --- | --- | --- |
| Magnesium Citrate | 32.4544 | Magnesium | 400 | mg |
| Tricalcium Citrate | 26.0211 | Calcium | 466 | mg |
| L-Carnitine L-Tartrate | 26.3389 | L-Carnitine | 1500 | mg |
| Maltodextrin | 5.8139 | Polysaccharide | 500 | mg |
| Ascorbic Acid | 1.4405 | Vitamin C | 100 | mg |
| Ferrous Gluconate | 1.8287 | Iron | 18 | mg |
| Citrus Bioflavonoid Complex | 0.2786 | Citrus | 25 | mg |
| Zinc Citrate | 0.5491 | Zinc | 15 | mg |
| Niacinamide | 0.3267 | Vitamin B3 | 25 | mg |
| Calcium D-Pantothenate | 0.1487 | Vitamin B5 | 10 | mg |
| D-Biotin 1% Trituration on Maltodextrin | 0.4120 | Vitamin B7 | 0.5 | mg |
| Cyanocobalamin, 01.% | 0.1712 | Vitamin B12 | 12 | mcg |
| 0.5% L.Selenomethionine | 0.7060 | Selenium | 140 | mcg |
| Pyridoxine HCl | 0.0787 | Vitamin B6 | 5 | mg |
| Lanolin | 0.0942 | Vitamin D3 | 17 | mcg |
| Thiamine Mononitrate | 0.2550 | Vitamin B1 | 15 | mg |
| Riboflavin | 0.2420 | Vitamin B2 | 17 | mg |
| Folic Acid | 0.0065 | Vitamin B9 | 0.4 | mg |
| Manganese Citrate | 0.1060 | Manganese | 2 | mg |
| Chromium Picolonate | 0.0048 | Chromium | 50 | mcg |
| Copper Gluconate | 0.1680 | Copper | 2 | mg |
| Reduced Glutathione | 2.0000 | Glutathione | 170 | mg |

To systematically document the effects that can be achieved by using the "InuCare" supplement, an evaluation of 25 participants treated with insulin has been carried out. The evaluation is based on well-proven methods that are used in quality-of-life surveys as well as previous experience with evaluations. The participants were initially contacted for their health and background status in a survey interview. An agreement was signed, and each participant received three months' supply of the "InuCare" supplement. After 1, 2 and 3 months, the participants answered a questionnaire related to their values of B-glucose and HbA1c as well as the average number of units of insulin taken by each participant. Furthermore, questions were asked about well-being, sleep, appetite, and energy.

Participant Descriptions

1. A 67-year-old male who has had type II diabetes for 18 years. The participant started taking insulin almost immediately as the tablets did not work well. The participant does not use a continuous blood glucose meter (CGM) but measures his blood sugar 4 times/day via capillary. He feels that his blood sugar is stable, and he takes the same number of units of insulin. Furthermore, he thinks that he has a good general condition, takes daily walks and sleeps about 6 hours a night but wakes up every two hours. At the first and second evaluations, the participant did not experience any change. His blood sugar levels and the number of units of insulin were the same as before he started the supplement. However, after three months, his sleep had improved. The participant was given a chance to participate in the evaluation for another two months to see if time affected the values, but blood sugar levels and the number of units of insulin have not changed. "My sleep has continued to be better."

2. A 41-year-old male who has been insulin dependent since he was diagnosed with Type I Diabetes 20 years ago. Participant uses CGM and insulin pump. Today, the participant is active by playing ice hockey three times a week and road cycling when it is not hockey season. He has a good appetite and sleeps well, about 7-8 hours a night. The participant feels that the energy goes up and down and has, for a year or so, felt more tired. At the first evaluation, the participant felt more alert. "It feels like the general condition is better in all areas." After two months, the participant slept better and felt more rested. He had a little less appetite and especially a smaller craving for sugar. Further, he reported better energy and a feeling of being more motivated to do difficult things. The participant has not responded to the third and final assessment despite several reminders.

3. 58-year-old male who was diagnosed with Type II Diabetes 7-8 years ago. The participant has little insulin production left and takes both tablets and insulin. The participant uses CGM. He is physically active 2-3 times a week with spinning and walking and he sleeps well, about 6 hours a night, but can be tired when he wakes up. The participant feels that he has a good general condition but can have difficult days with a lot of stress. At the first evaluation the participant felt much more alert, and he fell asleep more easily and slept "heavily". He had a lot more energy, could exercise more without getting so tired and lost 1 kg. His blood sugar dropped slightly; however, after two months, his sleep was still good, and he felt more alert in the body during the day. His HbA1c level dropped from 50 to 49 and he reduced his intake of the rapid acting type of insulin with two units. At the third evaluation, his sleep remained good, and he felt more alert in the body. The participant was pleased to have started the training. B-glucose and HbA1c did not change significantly; however, the number of units of long-acting insulin were lowered from 28 to 24.

4. A 31-year-old male who was diagnosed with type I diabetes about 2½ years ago. The participant uses CGM. The participant sleeps about 7-8 hours a night and if his blood sugar drops at night, he may feel sluggish when he wakes up. The participant thinks that the energy is quite good. He has a mobile job and when the weather permits, uses his bicycle to get to work. At the first evaluation after one month, he felt that his well-being had improved. After two months, he felt slightly stronger and fell asleep faster and slept more relaxed. His energy continued to improve week by week. At the third and final evaluation, the participant felt more rested when he woke up in the morning and the glucose values at night were more even. He also experienced greater motivation, less lactic acid and better endurance in his training. Blood sugar levels and HbA1c did not change.

5. 25-year-old male. Insulin-treated Diabetes Type I for 8 years. Participant has been taking insulin all the time and is using CGM. The participant sleeps about 6 hours a night and is tired in the morning and needs about 1 hour to wake up. The participant has a good appetite but does not eat breakfast. "I'm feeling more energetic, but I haven't been very physically active lately." At the first evaluation, the participant felt more alert except for one week when he had Covid. "Some mornings it was easier to get up and was also easier to get started with the training". The participant felt more energy in the body. After two months, the participant started with strength training. At the third evaluation, the participant reported going to the gym 4 times a week. His sleep was difficult to assess as there were disturbances in the house, but the hours he slept were perceived as good and qualitative. His blood sugar levels were a little lower during the night. Appetite was better and sometimes the participant ate breakfast. HbA1c had changed from a starting value of 47 to 43 to 45. The number of units of insulin was about the same.

6. A 29-year-old male who was diagnosed with type I diabetes at a very early age. Sleeps well, about 8-9 hours a night and is physically active several times a week. At the first evaluation, the participant felt that he had a little more energy, but above all he was much more insulin sensitive. "My sleep continued to be good, and my energy improved a little". After two months, the participant felt that the values looked much better, and he still felt alert and kept up with the training. "When your blood sugar is at a more even level, you automatically have more energy" The evaluation after three months showed that the positive feeling continued. B-glucose dropped from 9 to 6 and HbA1c from 52 to 47; however, the participant's goal is 45 and he is very close now.

Discussion

The participants' evaluations show that 4 out of 6 had lower values of HbA1c, while 2 had only a minor change. 2 to 3 participants were able to lower their insulin doses. Additionally, all 6 felt that their sleep was better and 4 out of 6 felt more alert. Getting better sleep and feeling more alert is a very positive attribute to face the morning work and/or physical activity since it can have a very positive effect on blood sugar and insulin needs.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

The invention claimed is:

1. A method for treating a subject with type I diabetes or type II diabetes or a subject diagnosed with prediabetes, the method comprising administering to the subject a therapeutically effective amount of a composition comprising:
vitamin B1,
vitamin B2,
vitamin B3,
vitamin B5,
vitamin B6,
vitamin B7,
vitamin B9,
vitamin B12, vitamin C,
vitamin $D_3$,
a pharmaceutically-acceptable compound of calcium,
a pharmaceutically-acceptable compound of magnesium,
a pharmaceutically-acceptable compound of zinc,
a pharmaceutically-acceptable compound of selenium,
a pharmaceutically-acceptable compound of iron, and
a pharmaceutically-acceptable compound of L-carnitine,
wherein the composition does not include vitamin E.

2. A method for treating a subject with type I diabetes or type II diabetes or a subject diagnosed with prediabetes, the method comprising administering to the subject a therapeutically effective amount of a composition comprising:
vitamin B1,
vitamin B2,
vitamin B3,
vitamin B5,
vitamin B6,
vitamin B7,
vitamin B9,
vitamin B12,
vitamin C,
vitamin $D_3$,
a pharmaceutically-acceptable compound of calcium,
a pharmaceutically-acceptable compound of magnesium,
a pharmaceutically-acceptable compound of zinc,
a pharmaceutically-acceptable compound of selenium,
a pharmaceutically-acceptable compound of iron, and
a pharmaceutically-acceptable compound of L-carnitine,
a pharmaceutically-acceptable compound of cobalt,
red beetroot extract, and a pectin.

3. The method of claim 1, wherein the composition treats one or more symptoms of type I diabetes or type II diabetes when compared to the same subject prior to the administration of the composition, wherein the symptom is selected from the group consisting of weight loss, polydipsia, polyuria, polyphagia, blurred vision, headache, fatigue, slow healing of cuts, itchy skin, and any combination thereof.

4. The method of claim 1, wherein the composition reduces the amount of insulin required by the subject.

5. The method of claim 1, wherein the composition further comprises red beetroot extract and a pectin.

6. The method of claim 1, wherein the pectin comprises sugarbeet pectin.

7. The method of claim 1, wherein the composition further comprises a pharmaceutically-acceptable compound of chromium and a pectin.

8. The method of claim 7, wherein the pectin comprises sugarbeet pectin.

9. The method of claim 1, wherein the composition further comprises
a therapeutically effective amount of
a pharmaceutically-acceptable compound of manganese,
a pharmaceutically-acceptable compound of chromium,
a pharmaceutically-acceptable compound of copper, and
reduced glutathione.

10. The method of claim 1, wherein the subject is further administered a marine omega 3 fatty acid, coenzyme Q10, or a combination thereof.

11. The method of claim 1, wherein the composition comprises vitamin B1 in an amount of from about 0.005 weight percent to about 0.10 weight percent of the composition;
vitamin B2 in an amount of from about 0.005 weight percent to about 0.10 weight percent of the composition;

vitamin B3 in an amount of from about 0.05 weight percent to about 0.50 weight percent of the composition;

vitamin B5 in an amount of from about 0.01 weight percent to about 0.50 weight percent of the composition;

vitamin B6 in an amount of from about 0.01 weight percent to about 0.50 weight percent of the composition;

vitamin B7 in an amount of from about 0.010 weight percent to about 0.50 weight percent of the composition;

vitamin B9 in an amount of from about 0.001 weight percent to about 0.10 weight percent of the composition;

vitamin B12 in an amount of from about 0.05 weight percent to about 0.50 weight percent of the composition;

vitamin C in an amount of from about 1.00 weight percent to about 10.00 weight percent of the composition;

vitamin D3 in an amount of from about 0.01 weight percent to about 0.50 weight percent of the composition;

a pharmaceutically-acceptable compound of calcium in an amount of from about 10.00 weight percent to about 35.00 weight percent of the composition;

a pharmaceutically-acceptable compound of magnesium in an amount of from about 15.00 weight percent to about 35.00 weight percent of the composition;

a pharmaceutically-acceptable compound of zinc in an amount of from about 0.10 weight percent to about 2.00 weight percent of the composition;

a pharmaceutically-acceptable compound of selenium in an amount of from about 0.01 weight percent to about 0.50 weight percent of the composition;

a pharmaceutically-acceptable compound of iron in an amount of from about 0.05 weight percent to about 5.00 weight percent of the composition; and a pharmaceutically-acceptable compound of L-carnitine in an amount of from about 10.00 weight percent to about 30.00 weight percent of the composition.

12. The method of claim 1, wherein the composition comprises vitamin B1 in an amount of from about 0.50 weight percent to about 3.00 weight percent of the composition;

vitamin B2 in an amount of from about 0.50 weight percent to about 3.00 weight percent of the composition;

vitamin B3 in an amount of from about 1.00 weight percent to about 3.00 weight percent of the composition;

vitamin B5 in an amount of from about 0.10 weight percent to about 2.00 weight percent of the composition;

vitamin B6 in an amount of from about 0.10 weight percent to about 2.00 weight percent of the composition;

vitamin B7 in an amount of from about 0.10 weight percent to about 3.00 weight percent of the composition;

vitamin B9 in an amount of from about 0.01 weight percent to about 0.10 weight percent of the composition;

vitamin B12 in an amount of from about 1.00 weight percent to about 10.00 weight percent of the composition;

vitamin C in an amount of from about 1.00 weight percent to about 10.00 weight percent of the composition;

vitamin D3 in an amount of from about 0.10 weight percent to about 1.00 weight percent of the composition;

a pharmaceutically-acceptable compound of calcium in an amount of from about 15.00 weight percent to about 25.00 weight percent of the composition;

a pharmaceutically-acceptable compound of magnesium in an amount of from about 5.00 weight percent to about 15.00 weight percent of the composition;

a pharmaceutically-acceptable compound of zinc in an amount of from about 1.00 weight percent to about 5.00 weight percent of the composition;

a pharmaceutically-acceptable compound of selenium in an amount of from about 0.10 weight percent to about 2.00 weight percent of the composition;

a pharmaceutically-acceptable compound of iron in an amount of from about 5.00 weight percent to about 20.00 weight percent of the composition;

a pharmaceutically-acceptable compound of L-carnitine in an amount of from about 10.00 weight percent to about 25.00 weight percent of the composition;

a pharmaceutically-acceptable compound of manganese in an amount of from about 0.10 weight percent to about 1.00 weight percent of the composition;

a pharmaceutically-acceptable compound of chromium in an amount of from about 0.001 weight percent to about 0.10 weight percent of the composition;

a pharmaceutically-acceptable compound of copper in an amount of from about 0.10 weight percent to about 2.00 weight percent of the composition; and glutathione or pharmaceutically-acceptable salt thereof in an amount of from about 5.00 weight percent to about 20.00 weight percent of the composition.

13. A method for treating a subject with type I diabetes or type II diabetes or a subject diagnosed with prediabetes, the method comprising administering to the subject a therapeutically effective amount of a composition comprising:

vitamin B1 in an amount of from about 0.005 weight percent to about 0.10 weight percent of the composition;

vitamin B2 in an amount of from about 0.005 weight percent to about 0.10 weight percent of the composition;

vitamin B3 in an amount of from about 0.05 weight percent to about 0.50 weight percent of the composition;

vitamin B5 in an amount of from about 0.01 weight percent to about 0.50 weight percent of the composition;

vitamin B6 in an amount of from about 0.01 weight percent to about 0.50 weight percent of the composition;

vitamin B7 in an amount of from about 0.010 weight percent to about 0.50 weight percent of the composition;

vitamin B9 in an amount of from about 0.001 weight percent to about 0.10 weight percent of the composition;

vitamin B12 in an amount of from about 0.05 weight percent to about 0.50 weight percent of the composition;

vitamin C in an amount of from about 1.00 weight percent to about 10.00 weight percent of the composition;

vitamin D3 in an amount of from about 0.01 weight percent to about 0.50 weight percent of the composition;

a pharmaceutically-acceptable compound of calcium in an amount of from about 10.00 weight percent to about 35.00 weight percent of the composition;

a pharmaceutically-acceptable compound of magnesium in an amount of from about 15.00 weight percent to about 35.00 weight percent of the composition;

a pharmaceutically-acceptable compound of zinc in an amount of from about 0.10 weight percent to about 2.00 weight percent of the composition;

a pharmaceutically-acceptable compound of selenium in an amount of from about 0.01 weight percent to about 0.50 weight percent of the composition;

a pharmaceutically-acceptable compound of iron in an amount of from about 0.05 weight percent to about 5.00 weight percent of the composition; and a pharmaceutically-acceptable compound of L-carnitine in an amount of from about 10.00 weight percent to about 30.00 weight percent of the composition.

14. A method for treating a subject with type I diabetes or type II diabetes or a subject diagnosed with prediabetes, the method comprising administering to the subject a therapeutically effective amount of a composition comprising:

vitamin B1 in an amount of from about 0.50 weight percent to about 3.00 weight percent of the composition;

vitamin B2 in an amount of from about 0.50 weight percent to about 3.00 weight percent of the composition;

vitamin B3 in an amount of from about 1.00 weight percent to about 3.00 weight percent of the composition;

vitamin B5 in an amount of from about 0.10 weight percent to about 2.00 weight percent of the composition;

vitamin B6 in an amount of from about 0.10 weight percent to about 2.00 weight percent of the composition;

vitamin B7 in an amount of from about 0.10 weight percent to about 3.00 weight percent of the composition;

vitamin B9 in an amount of from about 0.01 weight percent to about 0.10 weight percent of the composition;

vitamin B12 in an amount of from about 1.00 weight percent to about 10.00 weight percent of the composition;

vitamin C in an amount of from about 1.00 weight percent to about 10.00 weight percent of the composition;

vitamin D3 in an amount of from about 0.10 weight percent to about 1.00 weight percent of the composition;

a pharmaceutically-acceptable compound of calcium in an amount of from about 15.00 weight percent to about 25.00 weight percent of the composition;

a pharmaceutically-acceptable compound of magnesium in an amount of from about 5.00 weight percent to about 15.00 weight percent of the composition;

a pharmaceutically-acceptable compound of zinc in an amount of from about 1.00 weight percent to about 5.00 weight percent of the composition;

a pharmaceutically-acceptable compound of selenium in an amount of from about 0.10 weight percent to about 2.00 weight percent of the composition;

a pharmaceutically-acceptable compound of iron in an amount of from about 5.00 weight percent to about 20.00 weight percent of the composition;

a pharmaceutically-acceptable compound of L-carnitine in an amount of from about 10.00 weight percent to about 25.00 weight percent of the composition;

a pharmaceutically-acceptable compound of manganese in an amount of from about 0.10 weight percent to about 1.00 weight percent of the composition;

a pharmaceutically-acceptable compound of chromium in an amount of from about 0.001 weight percent to about 0.10 weight percent of the composition;

a pharmaceutically-acceptable compound of copper in an amount of from about 0.10 weight percent to about 2.00 weight percent of the composition; and glutathione or a pharmaceutically-acceptable salt thereof in an amount of from about 5.00 weight percent to about 20.00 weight percent of the composition.

\* \* \* \* \*